United States Patent [19]

Moyle et al.

[11] Patent Number: 5,508,261

[45] Date of Patent: Apr. 16, 1996

[54] ANALOGS OF GLYCOPROTEIN HORMONES HAVING ALTERED RECEPTOR BINDING SPECIFICITY AND ACTIVITY AND METHODS FOR PREPARING AND USING SAME

[75] Inventors: William R. Moyle, Piscataway, N.J.; Robert K. Campbell, Wrentham, Mass.; Gordon J. Macdonald, Piscataway, N.J.; Yi Han, Piscataway, N.J.; Yanhong Wang, Piscataway, N.J.

[73] Assignee: University of Medicine & Dentistry of New Jersey, Newark, N.J.

[21] Appl. No.: 425,673

[22] Filed: Apr. 18, 1995

Related U.S. Application Data

[63] Continuation of Ser. No. 184,408, Jan. 21, 1994, abandoned, which is a continuation-in-part of Ser. No. 108,845, Aug. 18, 1993, abandoned, which is a continuation of Ser. No. 717,151, Jun. 18, 1991, abandoned.

[51] Int. Cl.⁶ .................... A61K 38/24; A61K 38/22; C07K 14/575
[52] U.S. Cl. ................ 514/8; 530/397; 530/398
[58] Field of Search .................... 514/8; 530/397, 530/398

[56] References Cited

PUBLICATIONS

Matzuk et al., *The Journal of Biological Chemistry*, 264(5), 2409–2414, 1989.
Matzuk et al., *The Journal of Biological Chemistry*, 263(32), 17107–17111, 1988.
Bouslield et al. J. Biol. Chem. 263 12602–12067, 1988.
Rodgers et. al. J. Endocrinol. 129, 111.
Harlin et al. Fertil Steril. 46, 1055–1061, 1986.
Wallach et al. Fertil Steril 55, 478–480, 1991.
Schenher et al. Fertil Steril, 30 255–268, 1978.
Murphy et al. Endocrine Rev. 12, 27–44, 1991.
Campbell et al. Proc. Nat Acad, 88, 760–764, 1991.
Pierce et. al. Ann. Rev. Biochem, 50, 465–495, 1981.
Fiddes et al. Nature 286, 684–686, 1980.
Fiddes et. al. Nature 281 351—1980.
Keutmann. et al. Proc. Nat Acad, 84, 2038–2042, 1987.
Santa Colona et al. J. Biol Chem, 265, 5037–5042, 1990.
Schneyer et. al. Biochem, 27, 666–671, 1988.
Reddy et al. Proc. Nat. Acad. 83, 3644–3688, 1985.
Matzuk et. al. Proc Nat Acad, 84, 6354–6358, 1987.
Matzuk et al. Molec. Endocrinol., 2, 95–100, 1988.
Matzuk et al. J. Cell. Biol, 106, 1049–1059, 1988.
Moyle et. al. J. Biol. Chem., 265, 8511–8518, 1990.
Moyle et al. J. Biol Chem. 250 9163–9169, 1975.
Moyle et al. J. Receptor Research 8 419–436, 1988.

*Primary Examiner*—Howard E. Schain
*Assistant Examiner*—Pfynn Touzeau
*Attorney, Agent, or Firm*—Richard R. Muccino

[57] ABSTRACT

The present invention pertains to an alpha, beta-heterodimeric polypeptide having binding affinity to vertebrate luteinizing hormone (LH) receptors and vertebrate follicle stimulating hormone (FSH) receptors comprising a glycoprotein hormone alpha-subunit polypeptide and a non-naturally occurring beta-subunit polypeptide, wherein the beta-subunit polypeptide is a chain of amino acids comprising the following four joined subsequences:

(a) a first subsequence homologous to the amino acid sequence of residues 1–93 of the beta-subunit selected from the group consisting of human chorionic gonadotrophin (hCG), vertebrate luteinizing hormone (LH), vertebrate follicle stimulating hormone (FSH), and vertebrate thyroid stimulating hormone (TSH);

(b) a second subsequence homo logous to the amino acid sequence of residues 94–97 of the beta-subunit selected from the group consisting of human chorionic gonadotrophin (hCG) and vertebrate luteinizing hormone (LH);

(c) a third subsequence homologous to the amino acid sequence of residues 98-100 of the beta-subunit selected from the group consisting of human chorionic gonadotrophin (hCG), vertebrate luteinizing hormone (LH), vertebrate follicle stimulating hormone (FSH), and vertebrate thyroid stimulating hormone (TSH); and (d) a fourth subsequence homologous to the amino acid sequence of residues 101-110 of the beta-subunit of vertebrate follicle stimulating hormone.

8 Claims, 8 Drawing Sheets

ANALOGS OF GLYCOPROTEIN HORMONES HAVING ALTERED RECEPTOR BINDING SPECIFICITY AND ACTIVITY AND METHODS FOR PREPARING AND USING SAME

This is a continuation application of parent application Ser. No.: 08/184,408 filed on 21 Jan. 1994, now abandoned, which is a continuation-in-part application of parent application Ser. No. 08/108,845, filed on 18 Aug. 1993, now abandoned, which is a continuation application of patent application Ser. No. 07/717,151, filed 18 Jun. 1991, now abandoned.

BACKGROUND OF THE INVENTION

1. Field of the Invention

The present invention relates to glycoprotein hormone analogs having altered receptor binding specificity and activity. Specifically, the invention pertains to alpha, beta-heterodimeric polypeptides having binding affinity to follicle stimulating hormone (FSH) receptors and luteinizing hormone (LH) receptors. The residues important for receptor binding and specificity are located between Cys93 and Cys100 and Cys100 and Cys110 of hCG. These residues correspond to hFSH residues 87–94 and 94–104. A wide variety of alpha, beta-heterodimeric polypeptides can be made to alter the LH and FSH receptor binding activity and specificity of the polypeptides without disrupting their abilities to form alpha, beta-heterodimers or react with antibodies. This invention also pertains to methods for preparing these alpha, beta-heterodimeric polypeptides and the pharmaceutical compositions in which they may be employed.

The Reproductive Glycoprotein Hormones and Their Biological Actions

The glycoprotein hormone family consists of three alpha, beta heterodimeric glycoproteins found in the anterior pituitary gland where they are made and includes luteinizing hormone (LH), follicle stimulating hormone (FSH), and thyroid stimulating hormone (TSH). In some species, a glycoprotein hormone structurally similar to LH is found in the placenta wherein it is synthesized. In humans, this glycoprotein hormone is called human chorionic gonadotropin (hCG). In primates, significant quantities of all the hormones are also found as excretion products in urine. Urine from pregnant women serves as a convenient source of hCG. After menopause, when the secretion of LH and FSH from the anterior pituitary is greatly increased, significant quantities of LH and FSH are found in the urine and are termed human menopausal gonadotropins (hMG). Urine from menopausal women serves as an important source of LH and FSH activities. Both urinary hCG and hMG have important commercial uses. Unlike hCG, which interacts with LH receptors and only weakly with FSH receptors, hMG interacts with both LH and FSH receptors. The activity of hMG is due to the presence of multiple hormone species in the urinary extract.

Gonadotropins such as CG, LH, and FSH play a major role in the reproductive process while the structurally related hormone, TSH, is important for thyroid function. Both LH and FSH are essential for normal reproductive function and treatments to reduce LH activity result in infertility, termination of pregnancy, or both. FSH plays a crucial role in fertility. In the absence of sufficient FSH, women fail to have a normal menstrual cycle, i.e., a cycle in which a follicle develops to the point of ovulation. In polycystic ovarian disease, fertility can be restored by administration of FSH to women. The hormone hCG is important for maintenance of pregnancy. In males, the absence of LH and FSH is associated with infertility. The hormone LH is required for puberty and, in its absence, there is a failure to acquire the sexual attributes and fertility of an adult. The clinical activities of these hormones are reviewed extensively in several standard textbooks including that by Yen and Jaffe (1).

Both hCG and LH bind to luteinizing hormone receptors (LHR). In the testis, LHR are found primarily in the Leydig cells. In the ovary, LHR are found primarily in thecal, FSH-stimulated granulosa, and luteal cells. The major role of LH is to stimulate the formation of steroid hormones including the androgens testosterone and androstenedione (Leydig and thecal cells) and progesterone (FSH-stimulated granulosa, thecal, and luteal cells). LH also causes ovulation of mature follicles. While hCG is normally produced only by the placenta during pregnancy, due to its high affinity for LH receptors, the ease which it can be purified from urine, and its long biological half-life, hCG has been widely used as a substitute for LH. Important clinical uses for hCG include stimulation of fertility in males and induction of ovulation in females.

FSH binds to FSH receptors (FSHR) which are located primarily in the Sertoli cells of the testis and the granulosa cells of the ovaries. The primary roles of FSH are to stimulate the conversion of androgens (i.e., the steroids produced in response to LH stimulation of testicular Leydig cells and ovarian thecal cells) to estrogens, to promote the synthesis of inhibin and activin, to promote the development of Sertoli and granulosa cells, and to stimulate gamete maturation. The effect of FSH on granulosa cells leads to follicular maturation, a process during which the oocyte is prepared for ovulation and in which the granulosa cells acquire the ability to respond to LH. Follicle maturation is essential for the ability of LH to induce ovulation. Initiation of spermatogenesis requires FSH in addition to LH.

The differences in the effects of FSH and LH and the complex endocrine interactions between the two hormones cause them to have synergistic effects. For example, normal estrogen production is due to the effect of LH on androgen formation and the influence of FSH on the conversion of androgens to estradiol. This process is regulated by negative and positive feedback mechanisms wherein estradiol can inhibit FSH secretion and increase LH secretion from the pituitary gland. For this reason, the ratio of LH/FSH activity as well as the absolute hormone levels in blood are important for reproductive functions such as sperm production and ovulation of the proper number of oocytes during the menstrual and estrus cycles.

Uses of Glycoprotein Hormones and Desirability of Novel Hormone Analogs

Mixtures of FSH and LH activities (hMG) are routinely used in the treatment of human infertility, a condition affecting approximately 10% of all couples (2, 3). This particular combination therapy is necessary because gonadal support of gamete naturation is dependent upon the synergistic actions of both FSH and LH. Current treatment protocols requiring FSH and LH activity utilize urinary extracts from postmenopausal women. The use of these extracts is compromised by several factors including batch (4, 5) and supplier (6) variability, expense of treatment (7), and the risk of gonadal hyperstimulation, a potentially fatal side effect (8). These limitations potentially would be overcome through the use of hormone analogs which combine FSH and LH activity in the same molecule. Although there is a naturally occurring hormone, equine lutropin (eLH) which exhibits both FSH and LH activity in certain non-equine species (9), its practical application has been limited by side effects (8) and cross-species intolerance (3). Because the structural basis of the LH and FSH activity of eLH has not been understood, it has not been useful as a model for the engineering of mixed functions into hormones from other species. Further, it is not possible to reproducibly prepare eLH with different ratios of LH to FSH activity. In women with some forms of polycystic ovarian disease in which endogenous LH levels are elevated, it would be desirable to devise methods for producing glycoprotein hormone analogs which have a relatively higher ratio of FSH:LH activity. While protein engineering techniques have recently been reported to prepare analogs of hCG which bind with high affinity to FSH receptors (10), there has been no procedure for preparing glycoprotein hormones which bind well to LH and FSH receptors or which bind to LH and FSH receptors with a predictable ratio of FSH:LH activities.

Pathological changes in the ratios of FSH:LH are often associated with infertility (e.g., polycystic ovarian disease). Induction of ovulation can be influenced by the ratio of FSH:LH in serum (9) and it would be desirable to prepare analogs of glycoprotein hormones with any given ratio of LH/FSH activity. Presently, the only means of adjusting the ratios of LH to FSH in hormone preparations is to add FSH, LH, or hCG to them or to change the purification scheme. LH, FSH, and hCG have greatly differing half-lives and the ratio of hormone activity following in vivo administration of these preparations changes with time. Thus, mixtures of FSH and LH would gradually assume a higher ratio of FSH:LH activity following administration due to the longer half-life of FSH relative to LH. Since hCG has a much longer half-life than FSH, the ratio of FSH:LH activity of hFSH/hCG mixtures would gradually decrease after administration. It would be desirable to have analogs which contained a predefined ratio of LH to FSH activity in the same molecule. The ratio of FSH:LH activity in analogs with the capacity to bind to both LH and FSH receptors is expected to remain relatively constant after hormone administration. Analogs containing sequences derived from LH and FSH would have relatively short half-lives. In contrast, since the half-life of hCG is much longer than that of LH or FSH, if one were to use hCG as the primary structural component of these analogs, it should be possible to make analogs with a very long half-life. This would reduce the amounts of the analog needed for a biological effect. Small amounts of these analogs with approximately equal LH and FSH activity would be expected to be useful for inducing ovulation in women with hypothalamic amenorrhea and in males who fail to undergo puberty. Small amounts of analogs with lower ratios of LH/FSH activity would be expected to be useful clinically in cases where some endogenous LH is present such as inducing ovulation in women with polycystic ovarian disease or for increasing spermatogenesis in azospermic males who have some circulating LH. Previously, we have shown that it is possible to produce hCG analogs having very low LH activity and very high FSH activity (10). While these are primarily useful as FSH analogs, their LH activity could be increased only if they were mixed with hCG. Analogs of the human hormones with significant intrinsic LH and FSH activities have not yet been devised. In addition, based on the existing knowledge of the structure and functions of the glycoprotein hormones reviewed below, there is no obvious strategy which can enable these analogs to be devised.

Structures of the Glycoprotein Hormones

The structures of the glycoprotein hormones have been studied for many years and considerable information exists as to the relative roles of the hormone subunits (11). These hormones share a common alpha-subunit but differ in their hormone-specific beta-subunits which determine the biological and immunological properties of each hormone. The sequences of the subunits were determined several years ago and were confirmed from the base sequences of the subunit cDNA which had been cloned from pituitary and placental libraries (12, 13). Substitution of the alpha-subunits of any one hormone for that of another does not change the receptor binding properties of the new hormone. Substitution of the beta-subunit is accompanied by a change in the receptor binding specificity of the resulting hormone. Thus, when FSH beta-subunit is substituted for the LH beta-subunit, the recombined hormone acquires the properties of FSH and loses those characteristics of LH.

Several attempts have been made to identify portions of the alpha- and beta-subunits of the hormones which are responsible for their unique biological properties. Earlier studies were based on chemical modifications of the hormones (11). Modifications were described which reduced the biological activities of the hormones but no analogs were prepared which had switched LH and FSH receptor binding specificities. Due to the complexity of the hormones, this approach was unable to identify amino acid residues which were involved in ligand binding specificity. In an attempt to simplify the problem of identifying residues which are involved in ligand binding specificity, some investigators prepared synthetic peptides corresponding to partial sequences of the alpha- or beta-subunits and monitored their abilities to inhibit binding of $^{125}$I-hCG and $^{125}$I-hFSH to LH and FSH receptors. Synthetic peptides corresponding to amino acid residues of hCG-beta 38–57 or hFSH-beta 31–52 appear to have higher abilities than most other peptides to bind to these receptors (14, 15, 16). However, they have extremely low affinities for the receptors, an observation which precludes their practical use.

A breakthrough in the ability to make and characterize glycoprotein hormone analogs came in 1985 when genetically engineered mammalian cells were first shown to express biologically active hCG heterodimers (17). Since that time several laboratories have used mammalian cells to express glycoprotein hormone analogs which are capable of binding to receptors and inducing a biological function (10, 18–21). These analogs appear to be glycosylated similar to the naturally occurring hormones. While not important for hormone-receptor interaction, glycosylation of the hormones has been shown to be important for signal transduction in many species (22). In these procedures one introduces a "gene" that encodes the desired amino acid sequences into mammalian cells downstream of a promoter. Construction of these genes is a standard recombinant DNA procedure wherein the codons of the genes encoding the alpha or beta-subunits of the hormones are changed to encode amino acid residues of the desired analogs using the well established genetic code (23, 24). When these gene constructs are transfected into mammalian cells using standard protocols (23, 24), they direct the secretion of glycosylated hormone analogs into the culture media. These media can be assayed for the presence of immunological or biological activity (10, 21).

Using mammalian cell expression systems to make hormone analogs, Campbell et al. (10) engineered an analog which converted hCG from a hormone which bound to LH receptors to an analog which bound to FSH receptors and had only slightly higher affinity for LH receptors than FSH. Campbell et al. (10) were unsuccessful in obtaining analogs which had a high affinity for both LH and FSH receptors. As noted earlier, some naturally occurring analogs (i.e., eLH) can bind to both LH and FSH receptors and this property suggested that it should be possible to engineer human glycoprotein hormone analogs with the abilities to bind to both LH and FSH receptors. None of these analogs have been reported as yet.

One of the most interesting findings made from the studies of Campbell et al. (10) was that the region of hCG and hFSH which appeared to be important for receptor interaction was different from that which had been presumed to interact with the LH and FSH receptors based on the results of studies using synthetic peptides. Indeed, Campbell et al. (10) found that the amino acid residues which had been thought to control receptor binding specificity on the basis of studies using synthetic peptides (i.e., amino acids 38–57 of hCG and 32–51 Of hFSH) did not convey receptor binding activity in the intact hormone, the form which had highest affinity for the receptors.

BRIEF DESCRIPTION OF THE FIGURES

FIG. 6 illustrates that all the analogs can be detected in serum for several hours after they have been injected into rats. The value obtained at 1 hour was normalized to be 100% and the amounts of materials that remained after this time were expressed as a percentage of the amount at 1 hour. This method permits the relative stability of the materials to be seen. Urinary hCG, rhCG, and PRM1 are the most stable compounds and could be detected 24 or more hours after injection. The vertical bar in FIG. 6 extends to the upper limit of the standard error of the mean.

FIG. 8 also shows the abilities of 1 microgram of alpha subunit and 1 microgram of DG beta subunit to block binding of radioiodinated hCG and radioiodinated hFSH to these antisera. The methods used to obtain these data were identical to those described for FIG. 7 except that the alpha subunit or DG beta subunit were added in place of hCG and that radioiodinated hCG was substituted for radioiodinated hFSH in some samples. These data illustrate that serum from mice immunized with DG or G contains a large amount of antibody to the beta subunit since the DG beta subunit was much more effective than the alpha subunit in blocking the binding of radiolabeled hCG. These data also show that the alpha subunit was much more effective than the beta subunit in blocking the binding of radiolabeled hFSH to these same antisera. These data indicates that there are few, if any, antibodies to the FSH specific determinants present in DG and G. Thus, these compounds would not be expected to be antigenic in women.

SUMMARY OF THE INVENTION

Figure 1:
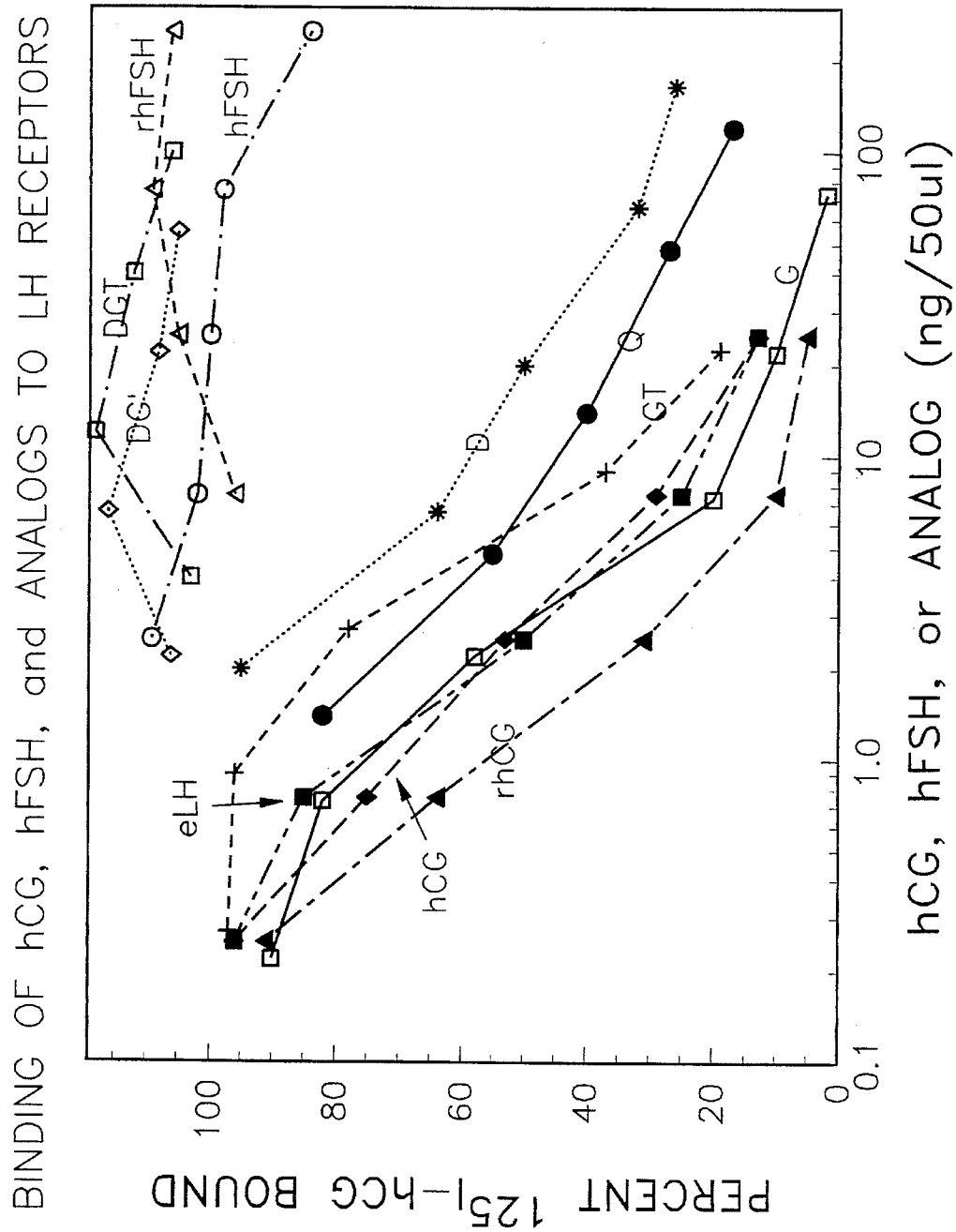
FIG. 1 depicts in graphic format the ability of hCG, hFSH, and the alpha, beta-heterodimeric polypeptide analogs of the present invention to inhibit binding of $^{125}$I-hCG to rat corpora luteal LH receptors.

The present invention pertains to an alpha, beta-heterodimeric polypeptide having binding affinity to vertebrate luteinizing hormone (LH) receptors and vertebrate follicle stimulating hormone (FSH) receptors comprising a glycoprotein hormone alpha-subunit polypeptide and a non-naturally occurring beta-subunit polypeptide, wherein the beta-subunit polypeptide is a chain of amino acids comprising the following four joined subsequences:

(a) a first subsequence homologous to the amino acid sequence of residues 1–93 of the beta-subunit selected from the group consisting of human chorionic gonadotrophin (hCG), vertebrate luteinizing hormone (LH), vertebrate follicle stimulating hormone (FSH), and vertebrate thyroid stimulating hormone (TSH);

(b) a second subsequence homologous to the amino acid sequence of residues 94–97 of the beta-subunit selected from the group consisting of human chorionic gonadotrophin (hCG) and vertebrate luteinizing hormone (LH);

(c) a third subsequence homologous to the amino acid sequence of residues 98–100 of the beta-subunit selected from the group consisting of human chorionic gonadotrophin (hCG), vertebrate luteinizing hormone (LH), vertebrate follicle stimulating hormone (FSH), and vertebrate thyroid stimulating hormone (TSH); and (d) a fourth subsequence homologous to the amino acid sequence of residues 101–110 of the beta-subunit of vertebrate follicle stimulating hormone.

DETAILED DESCRIPTION OF THE INVENTION

The present invention relates to glycoprotein hormone analogs having altered receptor binding specificity and activity. Applicants have discovered that the residues important for receptor binding and specificity in glycoprotein hormones are located between Cys93 and Cys100 and Cys100 and Cys110 of hCG. These residues correspond to hFSH residues 87–94 and 94–104. A wide variety of alpha, beta-heterodimeric polypeptides can be made to alter the LH and FSH receptor binding activity and specificity of the polypeptides without disrupting their abilities to form alpha, beta-heterodimers or react with antibodies. The finding that interactions between regions of hCG beta-subunit amino acids 94–97 and 101–106 (corresponding to hFSH beta-subunit amino acids 88–91 and 95–100) play a dominant role in determining hormone-receptor binding specificity was unexpected because 1) Keutmann H. T. et al. (14), Santa coloma and Reichert (15), and Schneyer, A. L., et al. (16) had shown that synthetic peptides containing beta-subunit amino acids from portions of the region 38–57 of hCG and 32–51 of hFSH were able to bind to LH and FSH receptors with low affinity and 2) Campbell et al. (10) had shown that residues 94–117 acted to cause an almost total shift in receptor binding specificity. The region containing amino acids 94–97 by itself did not influence receptor binding specificity and it was believed that modification of other residues in the 94–117 region of the molecule would also have an all- or-none effect on receptor binding specificity.

The alpha, beta-heterodimeric polypeptides of the present invention are "engineered" to alter the LH and FSH receptor binding activity and specificity of the polypeptides in vertebrates. Applicants have found that 1) the region of the hCG beta-subunit between 94–97 (i.e., "D" region) is most important for LH receptor binding activity and specificity, 2) the region of the hFSH beta-subunit between 100–106 (hCG numbering, i.e., "G" region) is most important for FSH binding activity and specificity and, 3) these regions ("D" and "G") of the beta-subunit are somewhat independent in activity. Substitution of a non-LH sequence in the "D" region will decrease binding of the polypeptide to the LH receptor. Substitution of a FSH sequence in the "G" region will increase binding of the polypeptide to the FSH receptor. Thus, it is possible to make modifications and substitutions in these regions to decrease the affinity of hCG for LH receptors and to dramatically increase the affinity of hCG for FSH receptors. The region of the beta-subunit between 1–93 and the choice of alpha-subunit does not appear to be important for LH and FSH binding activity and specificity. Hence analogs having a wide variety of activities can be made by altering the compositions of these two critical regions.

Generally, amino acid sequence variants will be substantially homologous with the relevant portion of the alpha, beta-heterodimeric polypeptides as set forth in Tables 1 and 2. Substantially homologous means that greater than about 70% of the primary amino acid sequence of the candidate polypeptide corresponds to the sequence of the relevant portion of the alpha, beta-heterodimeric polypeptide when aligned in order to maximize the number of amino acids residue matches between the two polypeptides. Alignment to maximize matches of residues includes shifting the amino and/or carboxyl terminus, introducing gaps as required or deleting residues present as inserts in the candidate polypeptide, or both. For example, see Tables 1 and 2 where the glycoprotein hormones and the alpha, beta-heterodimeric polypeptides are aligned for maximum homology. Typically, amino acid sequence variants will be greater than about 90% homologous with the corresponding sequences shown for the proteins in Tables 1 and 2.

Variants that are not hormonally-active fall within the scope of this invention, and include polypeptides that may or may not be substantially homologous with a sequence described herein but which are 1) immunologically cross-reactive with antibodies raised against the counterpart polypeptide or 2) capable of competing with such counterpart polypeptides for cell surface receptor binding. Hormonally active variants are produced by the recombinant or organic synthetic preparation of fragments or by introduction of amino acid sequence variations so that the molecule no longer demonstrates hormonal activity as defined herein.

Immunological or receptor cross-reactivity means that the candidate polypeptide is capable of competitively inhibiting the binding of the hormonally-active analogue to polyclonal antisera raised against the hormonally-active analogue. Such antisera are prepared in a conventional manner by injecting goats or rabbits S.C. with the hormonally active analogue or derivative in complete Freunds adjuvant, followed by booster intraperitoneal or S.C. injections in incomplete Freunds.

Variants that are not hormonally active but which are capable of cross-reacting with antisera to hormonally active polypeptides are useful a) as reagents in diagnostic assays for the analogues of their antibodies, b) when insolubilized in accord with known methods, as an agent for purifying anti-analogue anti-antibodies from anti-sera, and c) as an immunogen for raising antibodies to hormonally active analogues.

In accordance with the invention, the terminology "glycoprotein hormone" refers to human chorionic gonadotrophin (hCG), vertebrate luteinizing hormone (LH), vertebrate follicle stimulating hormone (FSH), and vertebrate thyroid stimulating hormone (TSH). The term "chimera" is used to designate a hormone analog which contains amino acid sequences derived from two or more different glycoprotein hormones.

In accord with the present invention, the alpha, beta-heterodimeric polypeptides comprise a glycoprotein hormone alpha-subunit polypeptide and a non-naturally occurring beta-subunit polypeptide. As set out above, the glycoprotein hormones share a common alpha-subunit. Substitution of the alpha-subunits of any one hormone for that of another does not significantly change the receptor binding properties of the new hormone. Accordingly, the alpha-subunit polypeptide in the present invention may be any vertebrate glycoprotein hormone alpha-subunit polypeptide. Nonlimiting examples of suitable alpha-subunit polypeptides include the alpha-subunits from human chorionic gonadotrophin (hCG), vertebrate luteinizing hormone (LH), vertebrate follicle stimulating hormone (FSH), and vertebrate thyroid stimulating hormone (TSH), and mixtures. In a preferred embodiment, the glycoprotein hormone alpha-subunit polypeptide may be selected from the group consisting of human chorionic gonadotrophin (hCG) and vertebrate luteinizing hormone (LH). In a more preferred embodiment, the glycoprotein hormone alpha-subunit polypeptide is human chorionic gonadotrophin (hCG). Preferably the glycoprotein hormone alpha-subunit polypeptide is a human polypeptide.

The beta-subunit of the alpha, beta-heterodimeric polypeptide is a non-naturally occurring beta-subunit polypeptide which is a chain of amino acids comprising four joined subsequences. The four joined subsequences are as follows:

(a) a first subsequence homologous to the amino acid sequence of residues 1–93 of the beta-subunit selected from the group consisting of human chorionic gonadotrophin (hCG), vertebrate luteinizing hormone (LH), vertebrate follicle stimulating hormone (FSH), and vertebrate thyroid stimulating hormone (TSH);

(b) a second subsequence homologous to the amino acid sequence of residues 94–97 of the beta-subunit selected from the group consisting of human chorionic gonadotrophin (hCG) and vertebrate luteinizing hormone (LH);

(c) a third subsequence homologous to the amino acid sequence of residues 98–100 of the beta-subunit selected from the group consisting of human chorionic gonadotrophin (hCG), vertebrate luteinizing hormone (LH), vertebrate follicle stimulating hormone (FSH), and vertebrate thyroid stimulating hormone (TSH);

(d) a fourth subsequence homologous to the amino acid sequence of residues 101–110 of the beta-subunit of vertebrate follicle stimulating hormone.

In one embodiment, the invention is directed to an alpha, beta-heterodimeric polypeptide having greater binding affinity for vertebrate follicle stimulating hormone (FSH) receptors than for vertebrate luteinizing hormone (LH) receptors comprising a glycoprotein hormone alpha-subunit polypeptide and a non-naturally occurring beta-subunit polypeptide, wherein the beta-subunit polypeptide is a chain of amino acids comprising the following four joined subsequences:

(a) a first subsequence homologous to the amino acid sequence of residues 1–93 of the beta-subunit selected from the group consisting of human chorionic gonadotrophin (hCG), vertebrate luteinizing hormone (LH), vertebrate follicle stimulating hormone (FSH), and vertebrate thyroid stimulating hormone (TSH);

(b) a second subsequence comprising 4 amino acids for residues 94–97;

(c) a third subsequence comprising 3 amino acids for residues 98–100; and (d) a fourth subsequence homologous to the amino acid sequence of residues 101–110 of the beta-subunit of vertebrate follicle stimulating hormone.

In another embodiment, the invention is directed to an alpha, beta-heterodimeric polypeptide having binding affinity to follicle stimulating hormone (FSH) receptors and luteinizing hormone (LH) receptors comprising a glycoprotein hormone alpha-subunit polypeptide and a non-naturally occurring beta-subunit polypeptide, wherein the beta-subunit polypeptide is a chimera comprised of amino acids 1–100 of any vertebrate glycoprotein hormone homologous to amino acids found in residues 1–100 of human chorionic gonadotropin and any 1–20 amino acids which binds LH receptors better than FSH receptors and has biological activity.

In a preferred embodiment, the alpha, beta-heterodimeric polypeptide is selected from the group consisting of "G", "DG"', "Q", "D", "GT", and "DGT" as set out in Tables 1 and 2. In a more preferred embodiment, the alpha, beta-heterodimeric polypeptide is "G".

Table 1 is a representation of the alpha, beta-heterodimeric polypeptides of the present invention using the one letter code and aligned in order to maximize the number of amino acids residue matches between the two polypeptides. Table 2 is a representation of the alpha, beta-heterodimeric polypeptides of the present invention using the three letter code. Abbreviations: A, Ala; C, Cys; D, Asp; E, Glu; F, Phe, G, Gly; H, His; I, Ile; K, Lys; L, Leu; M, Met; N, Asn; P, Pro; Q, Gln; R, Arg; S, Ser; T, Thr; V, Val; W, Trp; Y, Tyr.

TABLE 1

AMINO ACID SEQUENCES OF THE beta-SUBUNITS OF hCG, hLH, hFSH, AND THE alpha, beta-HETERODIMERIC POLYPEPTIDE ANALOGS

| POLYPEPTIDE ANALOG | | AMINO ACID SEQUENCES OF THE beta-SUBUNITS* |
|---|---|---|
| | | 10        20        30        40        50        60        70 |
| SEQ ID NO: 1 | hCG | SKEPLRP RCRPI N ATLAVEKEGCP VCIT VNI TI CAGY CP TMT R VL QGVLP ALPQVVCNYRDVRF ESI RLPGCP RG |
| SEQ ID NO: 2 | rhCG | SKEPLRP RCRPI N ATLAVEKEGCP VCIT VNI TI CAGY CP TMT R VL QGVLP ALPQVVCNYRDVRF ESI RLPGCP RG |
| SEQ ID NO: 3 | fFSH | NS CELTNI TI AI EKEE CRF CIS I NI TWCAGY CYTR DL VY KDP ARP KI QKTCTF KEL VYETVRVPGCAHH |
| SEQ ID NO: 4 | rhFSH | NS CELTNI TI AI EKEE CRF CIS I NI TWCAGY CYTR DL VY KDP ARP KI QKTCTF KEL VYETVRVPGCAHH |
| SEQ ID NO: 5 | eCG | SRGPLRP LCRPI N ATLAAEKEACPI CITF TTSI CAGY CP S MVR VMP AALP AI PQP VCTYRELRF ASI RLPGCP P G |
| SEQ ID NO: 6 | hTSH | FCI PTEYMTHI ERRE CAYCL TINTTI CA GYCMTRDI NGKL FLP KYAL SQDVCT YRDFI YRTVEI PQCP LH |
| SEQ ID NO: 7 | G | SKEPLRP RCRPI N ATLAVEKEGCP VCIT VNI TI CAGY CP TMT R VL QGVLP ALPQVVCNYRDVRF ESI RLPGCP RG |
| SEQ ID NO: 8 | DG' | SKEPLRP RCRPI N ATLAVEKEGCP VCIT VNI TI CAGY CP TMT R VL QGVLP ALPQVVCNYRDVRF ESI RLPGCP RG |
| SEQ ID NO: 9 | Q | SKEPLRP RCRPI N ATLAVEKEGCP VCIT VNI TI CAGY CP TMT R VL QGVLP ALPQVVCNYRDVRF ESI RLPGCP RG |
| SEQ ID NO: 10 | D | SKEPLRP RCRPI N ATLAVEKEGCP VCIT VNI TI CAGY CP TMT R VL QGVLP ALPQVVCNYRDVRF ESI RLPGCP RG |
| SEQ ID NO: 11 | GT | SKEPLRP RCRPI N ATLAVEKEGCP VCIT VNI TI CAGY CP TMT R VL QGVLP ALPQVVCNYRDVRF ESI RLPGCP RG |
| SEQ ID NO: 12 | DGT | SKEPLRP RCRPI N ATLAVEKEGCP VCIT VNI TI CAGY CP TMT R VL QGVLP ALPQVVCNYRDVRF ESI RLPGCP RG |

| POLYPEPTIDE ANALOG | | AMINO ACID SEQUENCES OF THE beta-SUBUNITS* |
|---|---|---|
| | | "D"        "G" |
| | | \|\|\|\|\|\|  \|\|\|\|\|\|\|\|\|\|\| |
| | | 80        90        100        110        120        130        140 |
| SEQ ID NO: 1 | hCG | VNPV VSYAVALS CQCAL CRRS T TDCGGP KDHPLT CDDP RF QDSS S SKAP PPSLPSPSRLP GPS DTPI LPQ |
| SEQ ID NO: 2 | rhCG | VNPV VSYAVALS CQCAL CRRS T TDCGGP KDHPLT CDDP RF QDSS S SKAP PPSLPSPSRLP GPS DTPI LPQ |
| SEQ ID NO: 3 | fFSH | ADSL YTYP VALQCHCGKCDS DS TDCT VRGL GPS YCS F GEMKE |
| SEQ ID NO: 4 | rhFSH | ADSL YTYP VALQCHCGKCDS DS TDCT VRGL GPS YCS F GEMKE |
| SEQ ID NO: 5 | eCG | VDPMVSF P VALS CHCGP CQI KT TDCGVF RDQPL ACAP QAS S S SKDPP S QPLTSTSTPTPGASRRSSHPLPIKTS |
| SEQ ID NO: 6 | hTSH | VAPY F SYP VALS CKCGKCDTDYSDCI HEAI KTNYCT KP QK S Y |
| SEQ ID NO: 7 | G | VNPV VSYAVALS CQCAL CRRS T TDCT VRGL GPS YCDDP R |
| SEQ ID NO: 8 | DG' | VNPV VSYAVALS CQCAL CDS DS TDCT VRGL GPS YCS F GE |
| SEQ ID NO: 9 | Q | VNPV VSYAVALS CQCAL CDS DS TDCGGP KDHPS YCS F GE |
| SEQ ID NO: 10 | D | VNPV VSYAVALS CQCAL CDS DS TDCGGP KDHPLT CDDP RF QDSS S SKAP PPSLPSPSRLP GPS DTPI LPQ |
| SEQ ID NO: 11 | GT | VNPV VSYAVALS CQCAL CRRS TTDCI HEAI KTNYCTKPQK S Y |
| SEQ ID NO: 12 | DGT | VNPV VSYAVALS CKCGKCDTDYSDCI HEAI KTNYCTKP QK S Y |

*NON-hCG DERIVED RESIDUES IN THE CHIMERAS ARE UNDERLINED

TABLE 2

AMINO ACID SEQUENCES OF THE beta-SUBUNITS OF hCG, hLH, hFSH, AND THE alpha.beta-HETERODIMERIC POLYPEPTIDE ANALOGS hCG (SEQ ID NO: 1)

SerLysGluProLeuArgProArgCysArgProIleAsnAlaThrLeuAlaValGluLysGluGlyCysProVal
CysIleThrValAsnIleThrIleCysAlaGlyTyrCysProThrMetThrArgValLeuGlnGlyValLeuPro
AlaLeuProGlnValValCysAsnTyrArgAspValArgPheGluSerIleArgLeuProGlyCysProArgGly
ValAsnProValValSerTyrAlaValAlaLeuSerCysGlnCysAlaLeuCysArgArgSerThrThrAspCys
GlyGlyProLysAspHisProLeuThrCysAspAspProArgPheGlnAspSerSerSerSerLysAlaProPro
ProSerLeuProSerProSerArgLeuProGlyProSerAspThrProIleLeuProGln hFSH (SEQ ID NO: 3)

AsnSerCysGluLeuThrAsnIleThrIleAlaIleGluLysGluGluCysArgPheCysIleSerIleAsnIle
ThrTrpCysAlaGlyTyrCysTyrThrArgAspLeuValTyrLysAspProAlaArgProLysIleGlnLysThr
CysThrPheLysGluLeuValTyrGluThrValArgValProGlyCysAlaHisHisAlaAspSerLeuTyrThr
TyrProValAlaLeuGlnCysHisCysGlyLysCysAspSerAspSerThrAspCysThrValArgGlyLeuGly
ProSerTyrCysSerPheGlyGluMetLysGlu eCG (SEQ ID NO: 5)

SerArgGlyProLeuArgProLeuCysArgProIleAsnAlaThrLeuAlaAlaGluLysGluAlaCysProIle
CysIleThrPheThrThrSerIleCysAlaGlyTyrCysProSerMetValArgValMetProAlaAlaLeuPro
AlaIleProGlnProValCysThrTyrArgGluLeuArgPheAlaSerIleArgLeuProGlyCysProProGly
ValAspProMetValSerPheProValAlaLeuSerCysHisCysGlyProCysGlnIleLysThrThrApsCys
GlyValPheArgAspGlnProLeuAlaCysAlaProGlnAlaSerSerSerSerLysAspProProSerGlnPro
LeuThrSerThrSerThrProThrProGlyAlaSerArgArgSerSerHisProLeuProIleLysThrSer hTSH (SEQ ID NO: 6)

PheCysIleProThrGluTyrMetThrHisIleGluArgArgGluCysAlaTyrCysLeuThrIleAsnThrThr
IleCysAlaGlyTyrCysMetThrArgAspIleAsnGlyLysLeuPheLeuProLysTyrAlaLeuSerGlnAsp
ValCysThrTyrArgAspPheIleTyrArgThrValGluIleProGlnCysProLeuHisValAlaProTyrPhe
SerTyrProValAlaLeuSerCysLysCysGlyLysCysAspThrAspTyrSerAspCysIleHisGluAlaIle
LysThrAsnTyrCysThrLysProGlnLysSerTyr

Analog "G" (SEQ ID NO: 7)

SerLysGluProLeuArgProArgCysArgProIleAsnAlaThrLeuAlaValGluLysGluGlyCysProVal
CysIleThrValAsnIleThrIleCysAlaGlyTyrCysProThrMetThrArgValLeuGlnGlyValLeuPro
AlaLeuProGlnValValCysAsnTyrArgAspValArgPheGluSerIleArgLeuProGlyCysProArgGly
ValAsnProValValSerTyrAlaValAlaLeuSerCysGlnCysAlaLeuCysArgArgSerThrThrAspCys
ThrValArgGlyLeuGlyProSerTyrCysAspAspProArg

Analog "DG" (SEQ ID NO: 8)

SerLysGluProLeuArgProArgCysArgProIleAsnAlaThrLeuAlaValGluLysGluGlyCysProVal
CysIleThrValAsnIleThrIleCysAlaGlyTyrCysProThrMetThrArgValLeuGlnGlyValLeuPro
AlaLeuProGlnValValCysAsnTyrArgAspValArgPheGluSerIleArgLeuProGlyCysProArgGly
ValAsnProValValSerTyrAlaValAlaLeuSerCysGlnCysAlaLeuCysAspSerAspSerThrAspCys
ThrValArgGlyLeuGlyProSerTyrCysSerPheGlyGlu

Analog "Q" (SEQ ID NO: 9)

SerLysGluProLeuArgProArgCysArgProIleAsnAlaThrLeuAlaValGluLysGluGlyCysProVal
CysIleThrValAsnIleThrIleCysAlaGlyTyrCysProThrMetThrArgValLeuGlnGlyValLeuPro
AlaLeuProGlnValValCysAsnTyrArgAspValArgPheGluSerIleArgLeuProGlyCysProArgGly
ValAsnProValValSerTyrAlaValAlaLeuSerCysGlnCysAlaLeuCysAspSerApsSerThrAspCys
GlyGlyProLysAspHisProSerTyrCysSerPheGlyGlu

Analog "D" (SEQ ID NO: 10)

SerLysGluProLeuArgProArgCysArgProIleAsnAlaThrLeuAlaValGluLysGluGlyCysProVal
CysIleThrValAsnIleThrIleCysAlaGlyTyrCysProThrMetThrArgValLeuGlnGlyValLeuPro
AlaLeuProGlnValValCysAsnTyrArgAspValArgPheGluSerIleArgLeuProGlyCysProArgGly
ValAsnProValValSerTyrAlaValAlaLeuSerCysGlnCysAlaLeuCysAspSerAspSerThrAspCys
GlyGlyProLysAspHisProLeuThrCysAspAspProArgPheGlnAspSerSerSerSerLysAlaProPro
ProSerLeuProSerProSerArgLeuProGlyProSerAspThrProIleLeuProGln

Analog "GT" (SEQ ID NO: 11)

SerLysGluProLeuArgProArgCysArgProIleAsnAlaThrLeuAlaValGluLysGluGlyCysProVal
CysIleThrValAsnIleThrIleCysAlaGlyTyrCysProThrMetThrArgValLeuGlnGlyValLeuPro
AlaLeuProGlnValValCysAsnTyrArgAspValArgPheGluSerIleArgLeuProGlyCysProArgGly
ValAsnProValValSerTyrAlaValAlaLeuSerCysGlnCysAlaLeuCysArgArgSerThrThrAspCys
IleHisGluAlaIleLysThrAsnTyrCysThrLysProGlnLysSerTyr

Analog "DGT" (SEQ ID NO: 12)

SerLysGluProLeuArgProArgCysArgProIleAsnAlaThrLeuAlaValGluLysGluGlyCysProVal
CysIleThrValAsnIleThrIleCysAlaGlyTyrCysProThrMetThrArgValLeuGlnGlyValLeuPro
AlaLeuProGlnValValCysAsnTyrArgAspValArgPheGluSerIleArgLeuProGlyCysProArgGly
ValAsnProValValSerTyrAlaValAlaLeuSerCysLysCysGlyLysCysAspThrAspTyrSerAspCys
IleHisGluAlaIleLysThrAsnTyrCysThrLysProGlnLysSerTyr

Figure 2:
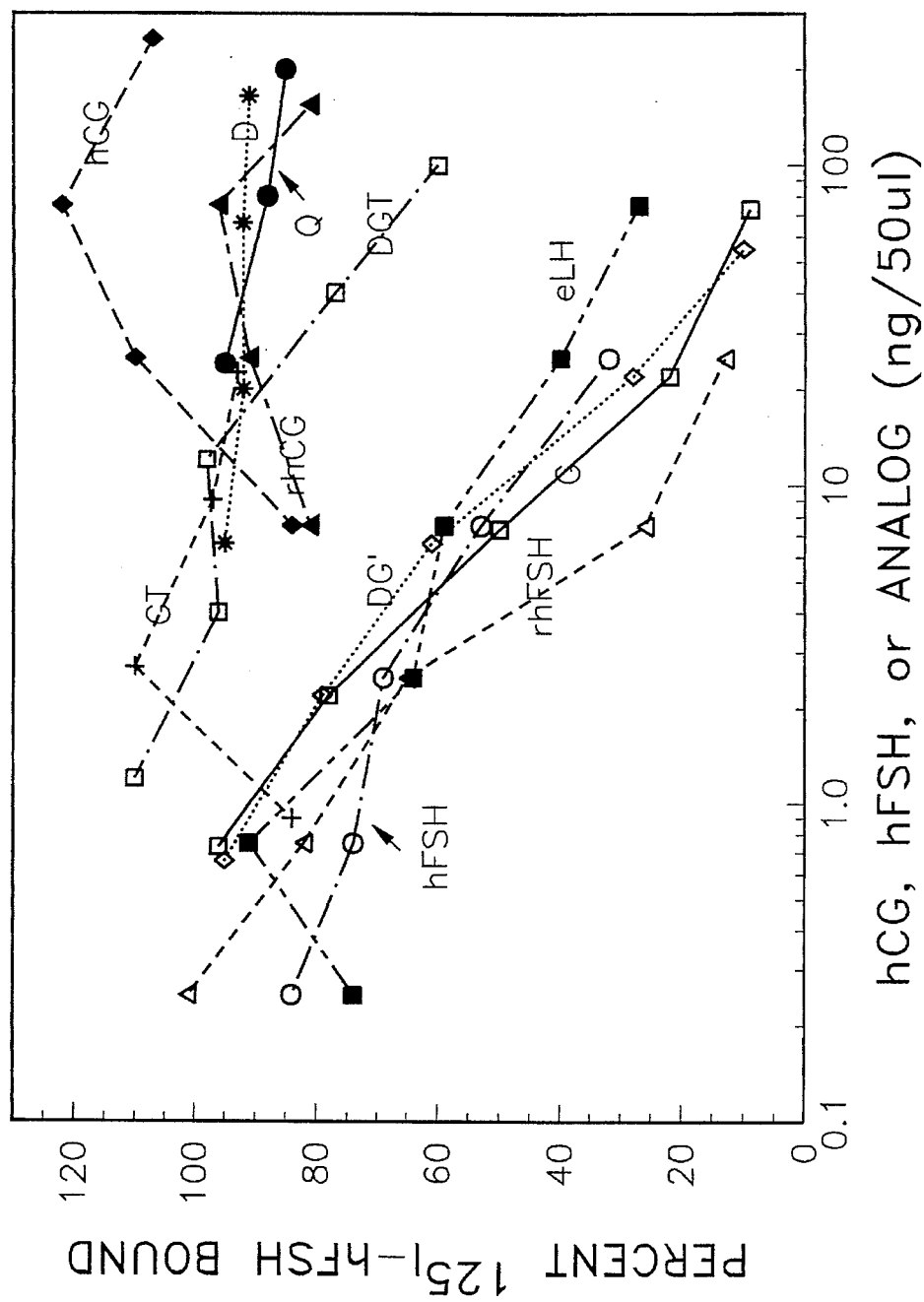
FIG. 2 depicts in graphic format the ability of hCG, hFSH, and the alpha, beta-heterodimeric polypeptide analogs of the present invention to inhibit binding of $^{125}$I-hFSH to bovine testes tissue homogenates.

The activities of alpha, beta-heterodimeric polypeptide analogs "DG'," "Q," "D," "GT," and "DGT" are illustrated in Table 3, FIG. 1, and FIG. 2 along with hCG, hFSH, and eLH controls. The properties of some of these analogs have been described previously (10).

TABLE 3

ACTIVITIES OF THE alpha, beta-HETERODIMERIC POLYPEPTIDE ANALOGS RELATIVE TO THAT OF hCG AND hFSH.

| ANALOG | LH RECEPTORS | FSH RECEPTORS |
|--------|--------------|---------------|
| rhCG   | 1.0          | N.D.          |
| rhFSH  | N.D.         | 1.0           |
| eCG    | 0.53         | 0.18          |
| G      | 0.62         | 0.29          |
| DG'    | N.D.         | 0.32          |
| Q      | 0.15         | N.D.          |
| D      | 0.065        | N.D.          |
| GT     | 0.33         | N.D.          |
| DGT    | N.D.         | N.D.          |

These values were obtained by dividing the concentration of analog required to inhibit $^{125}$I-hCG binding to rat luteal ovarian LH receptors or $^{125}$I-hFSH binding to bovine testes FSH receptors by 50% into that required for recombinant hCG and recombinant hFSH, respectively. The concentrations of the analogs were determined by sandwich immunoassay using antibodies B105 and A113. The term "N.D." means not determined because concentrations of analog were not employed high enough to detect 50% inhibition. This was because the amounts of hFSH needed to bind to LH Receptors are several orders of magnitude greater than that of hCG and vice versa the amounts of hCG needed to bind to FSH receptors are several orders of magnitude greater than that of hFSH.

These results show that it is possible to control the ratio of FSH:LH activity by modulating residues corresponding to hCG amino acids 94–99 and 101–109, hFSH amino acids 88–93 and 95–103, or hTSH amino acids 89–94 and 96–104. These regions are termed "D" and "G", respectively (c.f., Table 1). In general, substitution of a non-LH sequence in the "D" region decreases binding of the polypeptide to the LH receptor while substitution of a FSH sequence in the "G" region increases binding of the polypeptide to the FSH receptor. Analogs containing both "D" and "G" from hCG bind to LH receptors like hCG (10). Analogs containing both "D" and "G" from hFSH bind to FSH receptors like FSH (10). Analogs containing "D" from hCG and "G" from hFSH bind well to both LH and FSH receptors (Table 3, FIG. 1, and FIG. 2). Analogs containing "D" from hFSH and "G" from hCG bind to LH receptors with considerably lower potency than hCG (10, Table 3, FIG. 1, and FIG. 2) and do not bind to FSH receptors. Analogs with "D" from hCG and "G" from TSH (i e., "GT") bind to LH receptors but not to FSH receptors (Table 3, FIG. 1, and FIG. 2). Analogs with "D" and "G" from hTSH do not bind very well to either LH or FSH receptors (Table 3, FIG. 1, and FIG. 2).

These results show that it is possible to convert a human hormone into a molecule which binds to both LH and FSH receptors by using the "D" region from hCG and the "G" region from hFSH. Since replacement of the "D" region of hCG by residues from the "D" region of hFSH or hTSH dramatically lowers the ability of the analog to bind to LH receptors (i.e., compare hCG with analog "D" analog "G" with analog "DG'" and analog "GT" with analog "DGT"), it is clear that hFSH or hTSH substitutions in the "D" region which will make the analog less like hCG and will decrease its ability to bind to LH receptors. If the "G" region in these analogs is derived from hFSH, they will bind well to FSH receptors (i.e., compare analog "G" with analog "DG'"). Thus, as the residues in the "D" region are changed from those of hCG or any other hormone which binds to LH receptors to those of hFSH or hTSH, the ratios of LH:FSH activities will decrease and the analog will appear to behave more like FSH.

While the "D" region appears to have the greatest influence on binding of the analogs to LH receptors, the "G" region appears to have the greatest influence on binding of the analogs to FSH receptors. Thus, analog "G" binds FSH receptors better than analog "GT." Similarly, analog "DG'" binds FSH receptors better than analog "D" (Table 3, FIG. 1, and FIG. 2). Thus, as the residues in the "G" region are changed from hFSH or any other hormone which binds to FSH receptors to those of hCG or hTSH, the molecule will lose its ability to bind to FSH receptors, the ratios of LH:FSH activities will increase, and the analog will appear to behave more like hCG or LH.

By systematically varying the composition of residues in the "D" and "G" region between those of hCG, hFSH, and hTSH, it is possible to create a hormone analog which has any desired ratio of LH:FSH activity. Other regions of the hormone do not appear to have significant influence on receptor binding specificity (10).

Certain data suggest that the minimum sizes of regions "D" and "G" may be smaller than the sizes indicated. Thus in region "D" there are only 4 amino acids which differ between hCG and hFSH. Of these amino acids, only three are highly non-conserved (i.e., RRS/DSD). In region "G" there are 8 amino acids different between hCG and hFSH, however, it is clear that only 6 of these amino acid residues play an important role in receptor binding specificity. Thus, analog "Q" retains its ability to bind to LH receptors (Table 3, FIG. 1, and FIG. 2) even though it has two amino acid residues (i.e., 108 and 109) which are specifically found in the "G" region of hFSH, not hCG. On this basis, only 6 residues are believed to be critical in the "G" region.

The compounds of the present invention while effective in the form of the free form may be formulated and administered in the form of the therapeutically or pharmaceutically acceptable acid addition salts for purposes of stability, convenience of crystallization, increased solubility and the like. These acid addition salts include inorganic acid salts such as hydrochloric, hydrobromic, sulfuric, nitric, phosphoric, perchloric acid salts and the like; and organic acid salts such as acetic, trifluoroacetic, propionic, oxalic, hydroxyacetic, methoxyacetic, 2-hydroxypropanoic, 2-oxopropanoic, propanedioic, 2-hydroxy-butanedioic, benzoic, 2-hydroxybenzoic, 4-amino-2-hydroxybenzoic, 3-phenyl-2-propenoic, alpha-hydroxybenzeneacetic, methanesulfonic, ethanesulfonic, benzenesulfonic, toluenesulfonic, cyclohexanesulfamic, succinic, tartaric, citric, maleic, fumaric acid salts and the like. The preferred acid addition salts are chloride, oxalate and citrate. These acid addition salts can be prepared by conventional methods, such as by treatment of the free base of the inventive compound with the appropriate acid.

The compounds of the present invention, prepared in the free form, can be combined with a pharmaceutically acceptable carrier to provide a pharmaceutical composition. Suitable carriers for the free bases include propylene glycol-alcohol-water, isotonic water, sterile water for injection (USP), emulphor™-alcohol-water, cremophor-EL™ or other suitable carriers known to those skilled in the art.

The compounds of the present invention, prepared in the pharmaceutically acceptable acid addition salt form, can also be combined with a pharmaceutically acceptable carrier to provide a pharmaceutical composition. Suitable carriers for the acid addition salts include isotonic water, sterile water for injection (USP), alone or in combination with other solubilizing agents such as ethanol, propylene glycol, or other conventional solubilizing agents known to those skilled in the art.

Of course, the type of carrier will vary depending upon the mode of administration desired for the pharmaceutical composition as is conventional in the art. A preferred carrier is an isotonic aqueous solution of the inventive compound.

The compounds of the present invention can be administered to mammals, e.g., animals or humans, in amounts effective to provide the desired therapeutic effect. Since the activity of the compounds and the degree of the desired therapeutic effect vary, the dosage level of the compound employed will also vary. The actual dosage administered will also be determined by such generally recognized factors as the body weight of the patient and the individual hypersensitiveness of the particular patient. Thus, the unit dosage for a particular patient (man) can be as low as about 0.00005 mg/kg, which the practitioner may titrate to the desired effect.

The compounds of the present invention can be administered parenterally, in the form of sterile solutions or suspensions, such as intravenously, intramuscularly or subcutaneously in the carriers previously described. The compounds may also be administered orally, in the form of pills, tablets, capsules, troches, and the like, as well as sublingually, rectally, or transcutaneously with a suitable pharmaceutically acceptable carrier for that particular mode of administration as is conventional in the art.

For parental therapeutic administration, the compounds of the present invention may be incorporated into a sterile solution or suspension. These preparations should contain at least about 0.1% of the inventive compound, by weight, but this amount may be varied to between about 0.1% and about 50% of the inventive compound, by weight of the parental composition. The exact amount of the inventive compound present in such compositions is such that a suitable dosage level will be obtained. Preferred compositions and preparations according to the present invention are prepared so that a paranteral dosage unit contains from between about 0.5 milligrams to about 100 milligrams of the inventive compound.

The sterile solutions or suspensions may also include the following adjuvants: a sterile diluent, such as water for injection, saline solution, fixed oils, polyethylene glycol, glycerine, propylene glycol, or other synthetic solvent; antibacterial agents, such as benzyl alcohol or methyl paraben; antioxidants, such as ascorbic acid or sodium metabisulfite; chelating agents, such as ethylenediaminetetraacetic acid (EDTA); buffers, such as acetates, citrates or phosphates; and agents for the adjustment of tonicity, such as sodium chloride or dextrose. The parental preparations may be enclosed in ampules, disposable syringes, or multiple dose vials made of glass or plastic.

The compounds of the present invention can also be administered orally. For oral therapeutic administration, the compounds may be incorporated with excipients and used in the form of tablets, capsules, elixirs, suspensions, syrups, wafers, chewing gums and the like. These preparations should contain at least about 4% of the inventive compound, by weight, but this amount may be varied depending upon the particular dosage form from between about 4% to about 70% of the inventive compound, by weight of the oral composition. The exact amount of the compound present in the composition is such that a suitable dosage will be obtained. Preferred compositions and preparations according to the present invention are prepared so that an oral dosage unit form contains from between about 5 to about 300 milligrams of the inventive compound.

The tablets, pills, capsules, troches and the like may also contain the following adjuvants: a binder, such as microcrystalline cellulose, gum tragacanth or gelatine; an excipient, such as starch or lactose; a disintegrating agent, such as alginic acid, Primogel, corn starch and the like; a lubricating agent, such as magnesium stearate or Sterotex; a gliding agent, such as colloidal silicon dioxide; a sweetening agent, such as sucrose or saccharin; and a flavoring agent, such as peppermint, methyl salicylate or orange flavoring. When the dosage form is a capsule, it may additionally contain a liquid carrier such as a fatty oil. Other dosage unit forms may contain other materials which modify the physical form of the dosage unit, such as enteric coatings. Thus tablets or pills may be coated with sugar, shellac, or other enteric coating agents. A syrup may contain, in addition to the above adjuvants, sucrose as a sweetening agent, preservatives, dyes, coloring agents and flavoring agents.

It is especially advantageous to formulate the pharmaceutical compositions in dosage unit forms for ease of administration and uniformity of dosage. The term dosage unit forms as used herein refers to physically discrete units suitable for use as a unitary dosage, each unit containing a predetermined quantity of active ingredient calculated to produce the desired therapeutic effect in association with the pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Throughout this application, various publications have been referenced. The disclosures in these publications are incorporated herein by reference in order to more fully describe the state of the art.

The present invention is further illustrated by the following examples which are not intended to limit the effective scope of the claims. All parts and percentages in the examples and throughout the specification and claims are by weight of the final composition unless otherwise specified.

EXAMPLES

Preparation of "GT"

pSVLβ' was prepared by subcloning of the XhoI-BamHI fragment of pKBM-hCGβ' vector (10) into the XhoI-BamHI sites of pSVL (obtained from Pharmacia Co., Piscataway, N.J.). The approximately 3.6–3.7 Kbp PvuII-SstI fragment from pSVL-hCGβ' was ligated with the synthetic 25 oligonucleotide pair:

C Q C A L C R R S T T D C I H E A I K T N Y C T K P Q K S Y *
5'-
CTGTCAATGTGCACTCTGCCGCAGATCTACCACTGACTGCATACATGAAGCCATCAAGACAAACTACTGCACCAAACCTCAGAAGTCCTA
CTGAAGGCAGGTGAGCT-3'
and
3'-
GACAGTTACACGTGAGACGGCGTCTAGATGGTGACTGACGTATGTACTTCGGTAGTTCTGTTTGATGACGTGGTTTGGAGTCTTCAGGATG
ACTTCCGTCCAC-5'.

An aliquot of the ligation mixture was taken and used to transform DH5-alpha strain E. coli. (obtained from Bethesda Research Laboratories, Gaithersburg, Md.). Plasmid DNAs from ampicillin-resistant DH5-alpha clones were screened by digestion with BglII (which is unique to vectors containing the cassette) and EcoRI (which cuts in the vector). Positive clones were identified by the presence of two fragments (approximately 0.8 Kbp and 2.9 Kbp). The sequence in the coding region of one of these plasmids, which lacked most of the beta-subunit cDNA due to excision of the PvuII fragment, was confirmed by dideoxysequencing as described (10). The remainder of the beta-subunit cDNA (encoding hCGβ amino acids 1–87) was restored by ligation of the 2.3 Kbp PvuI-PvuII fragment of this vector and the 2.9 Kbp PvuI-PvuII fragment from pSVL-hCG-beta'. The ligation mixture was used to transform DH5-alpha strain E. coli. and ampicillin resistant clones were obtained. Miniprep plasmid DNA from these clones were digested with EcoRI and BglII, and DNA from positive clones exhibited fragments of approximately 2.5 Kbp and 2.9 Kbp. After the DNA was subjected to a dideoxy sequencing procedure to confirm that it encoded "GT" (Table 1), the plasmid DNA was then cotransfected into COS-7 cells (obtained from the American Type Culture Collection) along with pSVL-hCG-alpha, a pSVL-based plasmid encoding the human glycoprotein hormone alpha-subunit (10, 21), using a DEAE-dextran procedure (10). Beginning in 1–2 days and for a few days thereafter, the COS-7 cells produced significant amounts of the free subunits and the heterodimer. These were present in the culture media and heterodimer was detected using sandwich immunoassays employing monoclonal antibodies A113 and B105 (10). The protein was concentrated by ultrafiltration and monitored for its abilities to bind to LH and FSH receptors by radioligand receptor assays using $^{125}$I-hCG and $^{125}$I-hFSH as tracers and rat ovarian corpora lutea and bovine testes as sources of LH and FSH receptors as described (10).

Preparation of "G"

We have found that an alpha, beta-heterodimer composed of the alpha-subunit of hCG and an hCG/hFSH beta-subunit chimera termed "G" having the amino acid sequence illustrated in Table 1 has high affinity for LH and FSH receptors as shown by its ability to compete with radiolabeled hCG and/or hFSH for binding to these receptors (Table 3, FIGS. 1 and 2). This analog can be prepared in a variety of methods well-known to one versed in the art of molecular biology, one of which is described here. The cDNA for analog "GT" was digested with BglII and SstI and the 5.2–5.3 Kbp fragment was ligated with the oligonucleotides:

R S T T D C T V R G L G P S Y C D D P R *
5'-GATCTACCACTGACTGCACCGTGAGAGGCCTCGGGCCCTCTTACTGCGATGACCCGCGGTAGAGCT-3'
and
3'-ATGGTGACTGACGTGGCACTCTCCGGAGCCCGGGAGAATGACGCTACTGGGCGCCATC-5' using standard methods (23, 24). The ligation mixture was used to transform competent DH5-alpha strain E. coli. (23, 24). Transformed cells were selected by their abilities to grow on agar plates containing amphicillin. Ampicillin resistant colonies were chosen and plasmid minipreparations were made by the boiling lysis method (23, 24). The plasmid DNA was then tested for the presence of HindIII-ApaI endonuclease restriction sites. Plasmid DNA having the desired sequences was cleaved into three fragments (approximately 0.8 Kbp, 1.1 Kbp, and 3.4 Kbp). After the DNA was subjected to a dideoxy sequencing procedure to confirm that it encoded "G" (Table 1), the plasmid DNA was then cotransfected into COS-7 cells (obtained from the American Type Culture Collection) along with pSVL-hCG-alpha, a pSVL-based plasmid encoding the alpha-subunit (10, 21), using a DEAE-dextran procedure (10, 21, 23, 24). Beginning in 1–2 days and for a few days thereafter, the COS-7 cells produced significant amounts of the free subunits and the heterodimer. These were present in the culture media and heterodimer was detected using sandwich immunoassays employing monoclonal antibodies A113 and B105 (10). The protein was concentrated by ultrafiltration and monitored for its abilities to bind to LH and FSH receptors by radioligand receptor assays using $^{125}$I-hCG and $^{125}$I-hFSH as tracers and rat ovarian corpora lutea and bovine testes as sources of LH and FSH receptors as described (10).

Preparation of "D" and "DG'" and "Q"

Preparations of analogs "D" and "DG'" have been described previously (10) and are the same as those of analogs CF94–97 and CF94–114 in that report, respectively. Analog "Q" was prepared from the expression vector encoding analogs "D" and CF108–114 (10) by digesting them with PpuMI, separating the fragments on agarose gels, and ligating the large fragment obtained from CF108–114 with the small fragment obtained from "D." The resulting plasmid was then cotransfected into COS-7 cells along with pSVL-hCG-alpha and the media assayed for the presence of the analogs using an A113-B105 sandwich immunoassay as described (10).

Preparation of "DGT"

Plasmid pSVL-hCGβ' was sequentially digested with SstI and PvuII and the 3.6 Kbp fragment was ligated with the synthetic DNA cassette formed by annealing the following oligonucleotides:

```
C K C G K C N T D Y S D C I H E A I K T N T C T K P Q K S Y *
```
5'-
CTGTAAGTGTGGCAAGTGCAATACTGACTACAGTGACTGTATACATGAAGCCATCAAGACAAACTACTGCACCAAACCTCAGAAGTCCT
ACTGAAGGCAGGTGAGCT-3'
and
3'-
GACATTCACACCGTTCACGTTATGACTGATGTCACTGACATATGTACTTCGGTAGTTCTGTTTGATGACGTGGTTTGGAGTCTTCAGGA
TGACTTCCGTCCAC-5'.

The ligation mixture was used to transform DH5Á E. coli. and miniprep plasmid DNA obtained from ampicillin resistant colonies was screened for the presence of an approximately 0.6Kbp fragment released by digestion with AccI. After DNA sequencing was performed to confirm that the construct encoded the desired sequence, it was cut with PvuII and ligated with the 1.6 Kbp fragment of pSVL-hCGβ'. The ligation product was transformed into DH5-alpha strain E. coli. and positive clones were selected. Plasmid DNA was prepared by boiling lysis and digested with EcoNI and XhoI. DNA which had the insert in the correct orientation produced fragments approximately 2.6 Kbp, 1.7 Kbp, 0.5 Kbp, 0.25 Kbp, and 0.15 Kbp. The plasmid DNA was then cotransfected into COS-7 cells (obtained from the American Type Culture Collection) along with pSVL-hCG-alpha, a pSVL-based plasmid encoding the alpha-subunit (10, 21), using a DEAE-dextran procedure (10, 21, 23, 24). Beginning in 1–2 days and for a few days thereafter, the COS-7 cells produced significant amounts of the free subunits and the heterodimer. These were present in the culture media and heterodimer was detected using sandwich immunoassays employing monoclonal antibodies A113 and B105 (10). The concentration of the protein was concentrated by ultrafiltration and monitored for its abilities to bind to LH and FSH receptors by radioligand receptor assays using $^{125}$I-hCG and $^{125}$I-hFSH as tracers and rat ovarian corpora lutea and bovine testes as sources of LH and FSH receptors as described (10).

The procedures set out below produce the alpha, beta-heterodimeric polypeptides in a transient fashion. As is well known in the art, vectors other than pSVL can be chosen which will enable the protein to be expressed in a stable fashion in larger quantities. The DNA sequences described above can be excised from pSVL and then subcloned into any other expression vector. Cell types other than COS-7 cells can be used to express the analogs. These include virtually any eucaryotic cell for which an expression vector is known or can be devised and include mammalian cells, insect cells, yeast cells, fungal cells, and plant cells.

The abilities of the analogs to inhibit binding of $^{125}$I-hCG to rat corpora luteal LH receptors was performed by procedures similar to those described previously. Immature rats were given injections of pregnant mares serum gonadotropin and hCG to induce the formation of corpora lutea. The ovaries were removed from the animals, homogenized, and stored at a concentration of approximately 5mg homogenate tissue in 100 ul buffer (25).

The abilities of the analogs to inhibit binding of $^{125}$I-hFSH to bovine testes tissue homogenates was performed by procedures similar to those described previously (10).

FIGS. 1 and 2 depict in graphic format the ability of hCG, hFSH, and the alpha, beta-heterodimeric polypeptide analogs of the present invention to inhibit binding of $^{125}$I-hCG to rat corpora luteal LH receptors and binding of $^{125}$I-hFSH to bovine testes tissue homogenates, respectively.

The in vivo properties of the analogs termed DG also known as CF94–117, G also known as CF 101–109, and PRM1 have also been studied. DG is the α,β heterodimer that has the human-subunit and the β-subunit with hCG residues 1–93 and hFSH residues 88–111 in place of their hCG counterparts at 94–117.

Figure 3:
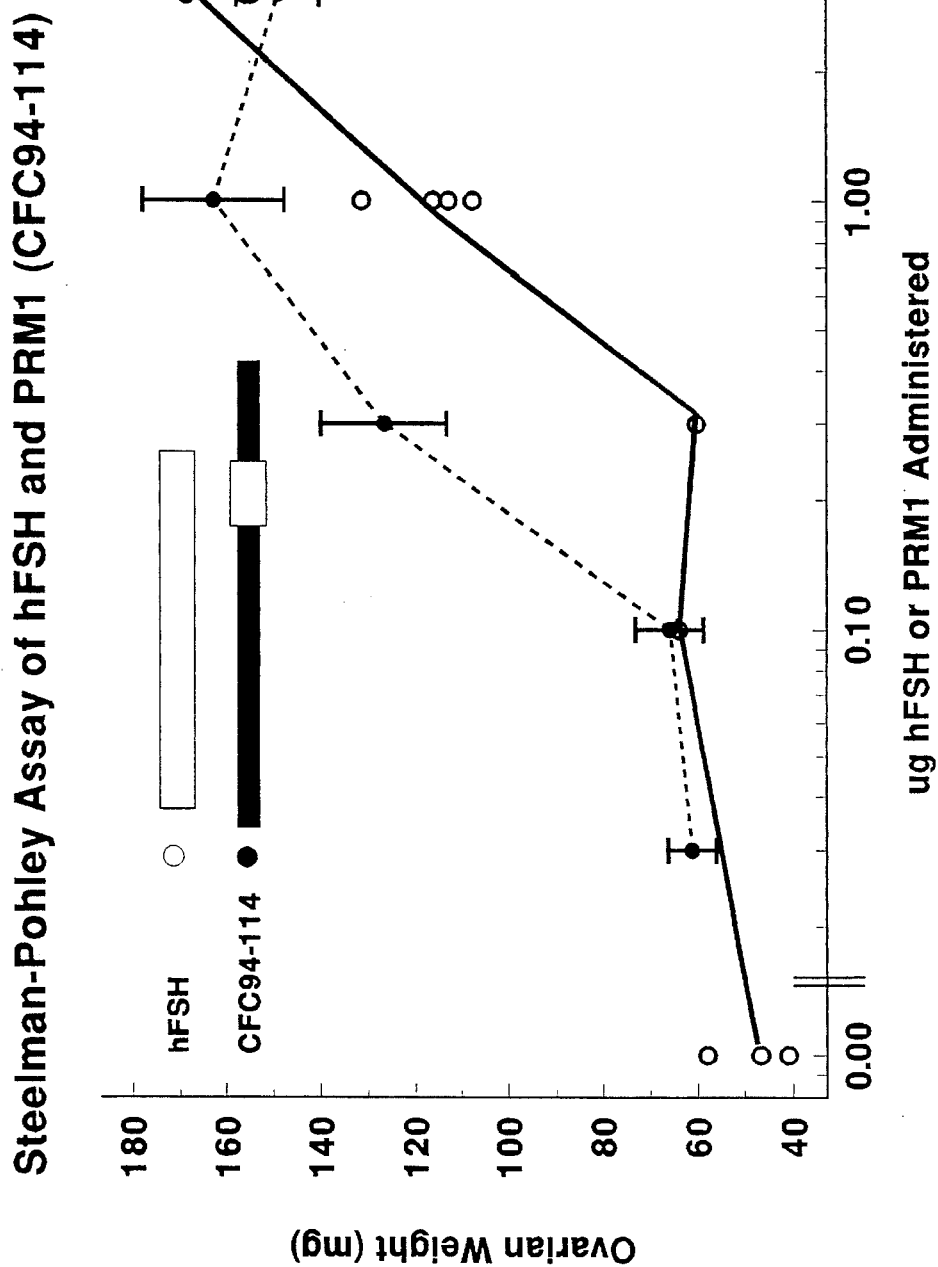
FIG. 3 illustrates the ability of PRM1 (CFC94–114) to stimulate the growth of immature rat ovaries relative to hFSH. Dose response curves from four different experiments involving hFSH are illustrated for comparison with the activity of PRM1. All of the hFSH dose response curves are not statistically significantly different from one another whereas that for PRM1 can be seen to be 3–4 fold shifted to the left. This shift indicates that PRM1 is three-four fold more active than hFSH in this in vivo assay. This experiment was performed using sexually immature 21 day old female rats. The total amount of hFSH or PRM1 indicated by the values on the abscissa was mixed with 50 IU of hCG. Thus, for example, when a dose of 0.3 micrograms is indicated on the abscissa, 0.3 micrograms of hFSH or PRM1 was mixed with 50 IU of hCG. One sixth of this mixture was injected into the rats subcutaneously (s.c.) twice per day for three days. When a dose of 1 microgram is indicated, 1 microgram of either hFSH or PRM1 was mixed with 50 IU of hCG. One sixth of this mixture was injected into the rats (s.c.) twice per day for three days. When a dose of 3 micrograms is indicated, 3 micrograms of either hFSH or PRM1 was mixed with 50 IU of hCG. As before, one sixth of this mixture was injected into the rats (s.c.) twice per day for three days. When 0 micrograms of hFSH or PRM1 was used, the rats received a total of 50 IU of hCG divided into six equal doses in which one dose was given (s.c.) twice per day for three days. On the fourth day all the rats were sacrificed and the weights of their ovaries were determined. From these data in FIG. 3, it can be seen that a dose of 0.3 micrograms of PRM1 was as effective as a dose of 1 microgram of hFSH. The vertical bars extend to the limits of the standard deviation.
Figure 4:
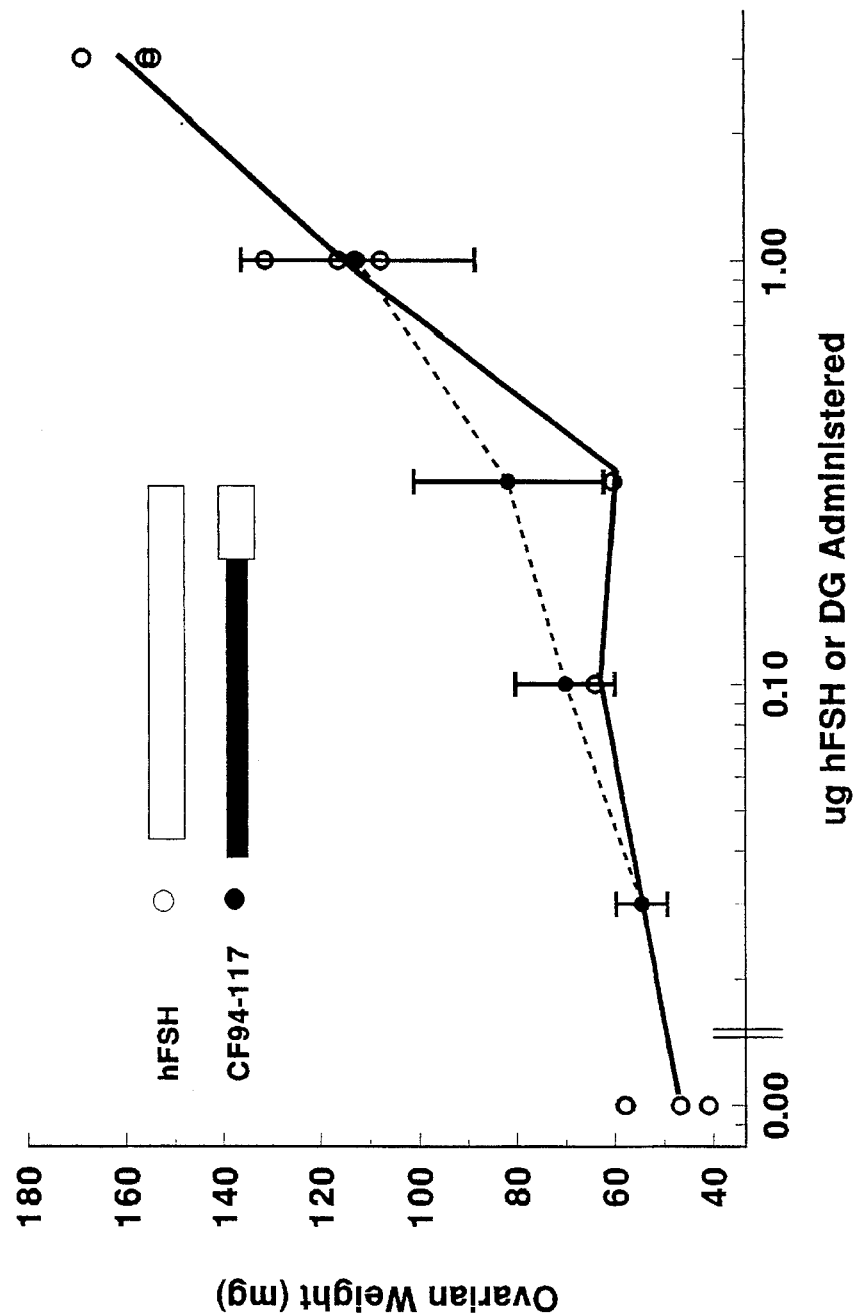
FIG. 4 illustrates the relative potencies of hFSH and DG (CF94-117). The procedure to obtain the potencies of these hormones is identical to that desribed for FIG. 3 except that DG was used in place of PRM1. It can be seen in FIG. 4 that the relative potencies of hFSH and DG are similar in vivo.
Figure 5:
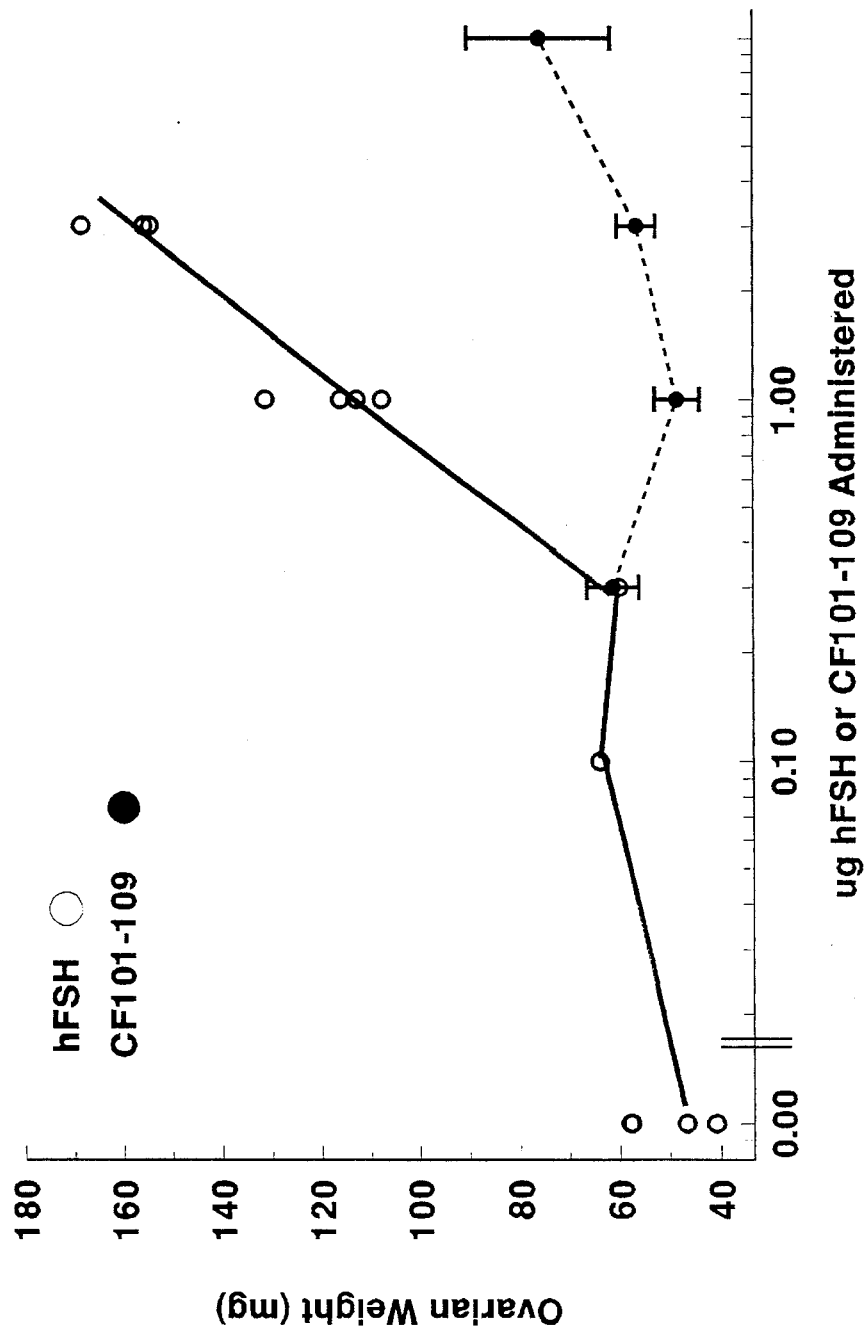
FIG. 5 illustrates the relative potencies of hFSH and G (CF101–109). The procedure to obtain the potencies of these hormones is identical to that described for FIG. 3 except that G was used in place of PRM1. It can be seen in FIG. 5 that G is active in stimulating ovarian weight gain but is less active than hFSH in this assay.

As illustrated in FIGS. 3-5, chimeras of hCG and hFSH that are active in vitro are also active in vivo. Thus, PRM1, DG, and G were able to increase the ovarian weights of sexually immature female rats ovaries. The classical Steelman-Pohley assay [Steelman, S. L. and Pohley, F. M. (1953) of the follicle stimulating hormone based on the augmentation with human chorionic gonadotropin was used. Endocrinology 53: 604–616] that is an accepted parameter of FSH activity. PRM1 was 3–4 fold more active than hFSH. DG was approximately equally active. G was less active than hFSH.

Figure 6:
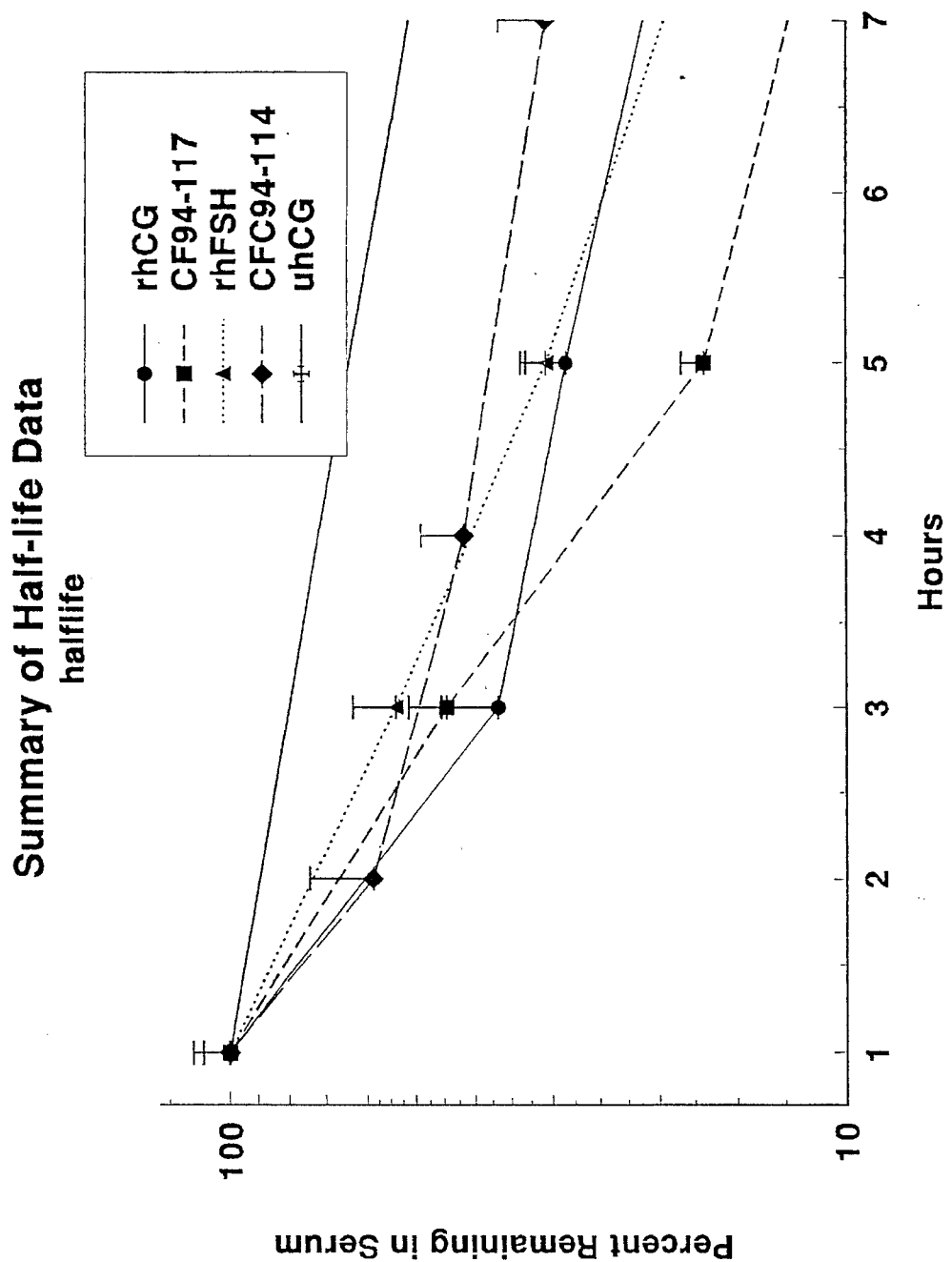
FIG. 6 illustrates the half lives of hCG isolated from the urine of pregnant women (uhCG), hCG made in cell culture (rhCG), hFSH made in cell culture (rhFSH), DG (CF94-117) made in cell culture, and PRM1 (CFC94-114) made in cell culture. In these experiments, 5-15 micrograms of the proteins were injected intravenously into the external jugular vein of rats that had been anesthetized with ether. At the times indicated on the abscissa, the rats were reanesthetized and 0.2 ml of blood withdrawn and allowed to clot. The serum from this blood was obtained by centrifuging the clotted blood at 2000×g for 30 minutes. For measurements of hCG, DG, and PRM1, aliquots of the serum (0.1–50 microliters) were used in sandwich immunoassays employing A113 as a capture antibody and radioiodinated B105 as a detection antibody. hCG purified from urine was used as a standard curve to measure hCG, DG, and PRM1. For measurements of hFSH, aliquots of the serum (0.1–50 microliters) were used in sandwich immunoassays employing A113 as a capture antibody and radioiodinated B602 as detection antibody. hFSH purified from tissue culture medium was used as a standard to measure hFSH.

As illustrated in FIG. 6, the half-life of DG is approximately the same as that of hFSH and less than that of urinary hCG. The half-life of PRM1 appears to be slightly longer. These half-live studies were performed by injecting approximately 5–15 μg of hormones i.v. into a rat and then drawing samples at various times (indicated on the figure). The amount of material in serum was estimated by sandwich immunoassay employing antibodies A113 for capture and radioiodinated B105 for detection of hCG, DG, G, and PRM1. For hFSH we used a sandwich assay based on A113 and radioiodinated B602. These assays have been described in other patent applications.

Figure 7:
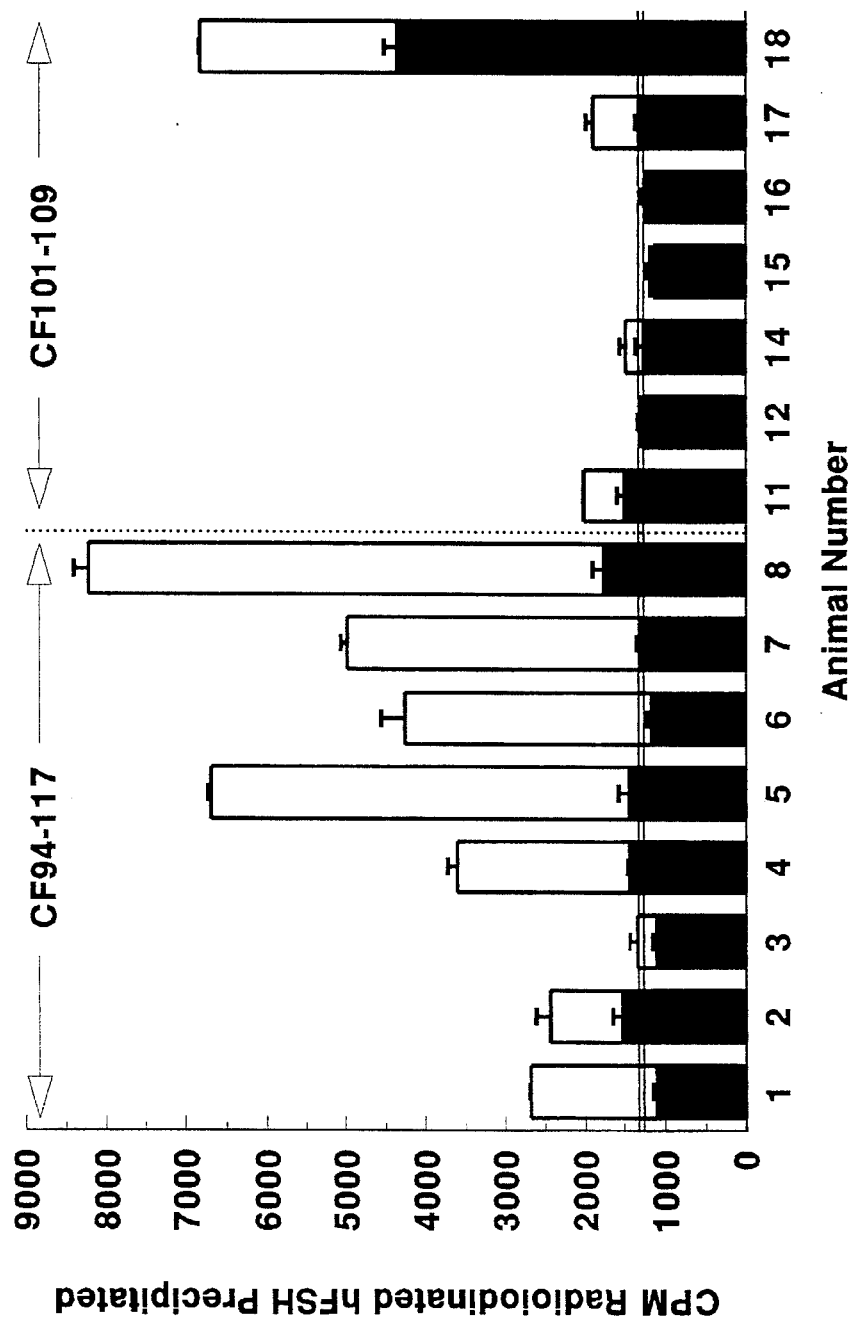
FIG. 7 illustrates the antigenicity of DG (CF94–117) and G (CF101–109) in mice. Approximately 1 microgram of DG or 1 microgram of G were injected subcutaneously in Freund's complete Adjuvant (first injection) and once per month for 4 months using Freund's incomplete adjuvant into BALB/cxRIII mice. Blood was drawn from the orbital sinus and permitted into a capillary pipette and centrifuged in the pipette at 2000×g for 3 minutes to obtain the serum. The data on the left side of the broken vertical line refer to the antigenicity of DG and those on the right side of the vertical line refer to the antigenicity of G. One tenth microliter of sera from the mice was diluted into 25 microliters of solution A. Solution A consisted of 0.9% NaCl solution containing 1 mg/ml of bovine serum and 0.02M sodium phosphate buffer (pH 7.2). Next, 25 microliters of solution A containing 50 nCi of radioiodinated hFSH (approximately 1 ng) were added and the mixture incubated for 30 minutes at 37° C. To this mixture was added goat anti-mouse immunoglobulin (2 micrograms) that had been obtained from Cappel, Organon, and the mixture incubated at 37° C for 90 minutes or at 4° C for 16 hours. To this mixture was added 100 microliters of a 1% suspension of IgGsorb, The Enzyme Center, and the mixture was incubated for 30 minutes at 22° C. Finally, 3 mls of solution A were added, the mixture was centrifuged for 10 minutes at 2000×g, and the supernate aspirated and discarded. The radioactivity in the pellet was determined in a gamma counter that had approximately 70% efficiency for the radioiodine used. The blank value is determined using the serum from mice that had not been immunized (pre or preimmunization). Values illustrated in FIG. 7 were determined in the absence (open bars) and presence of 1 microgram of hCG added to the serum prior to the addition of the radiolabeled hFSH. These values illustrate that sera from mice immunized with DG and G can bind to hFSH. In nearly all cases, the binding of radiolabeled hFSH can be totally inhibited by the presence of hCG. This inhibition indicates that the antibodies in the serum bind radioiodinated hFSH through its conserved alpha subunit. This inhibition also indicates that most antibodies have little, if any, affinity for the parts of the hFSH beta subunit found in DG and G.
Figure 8:
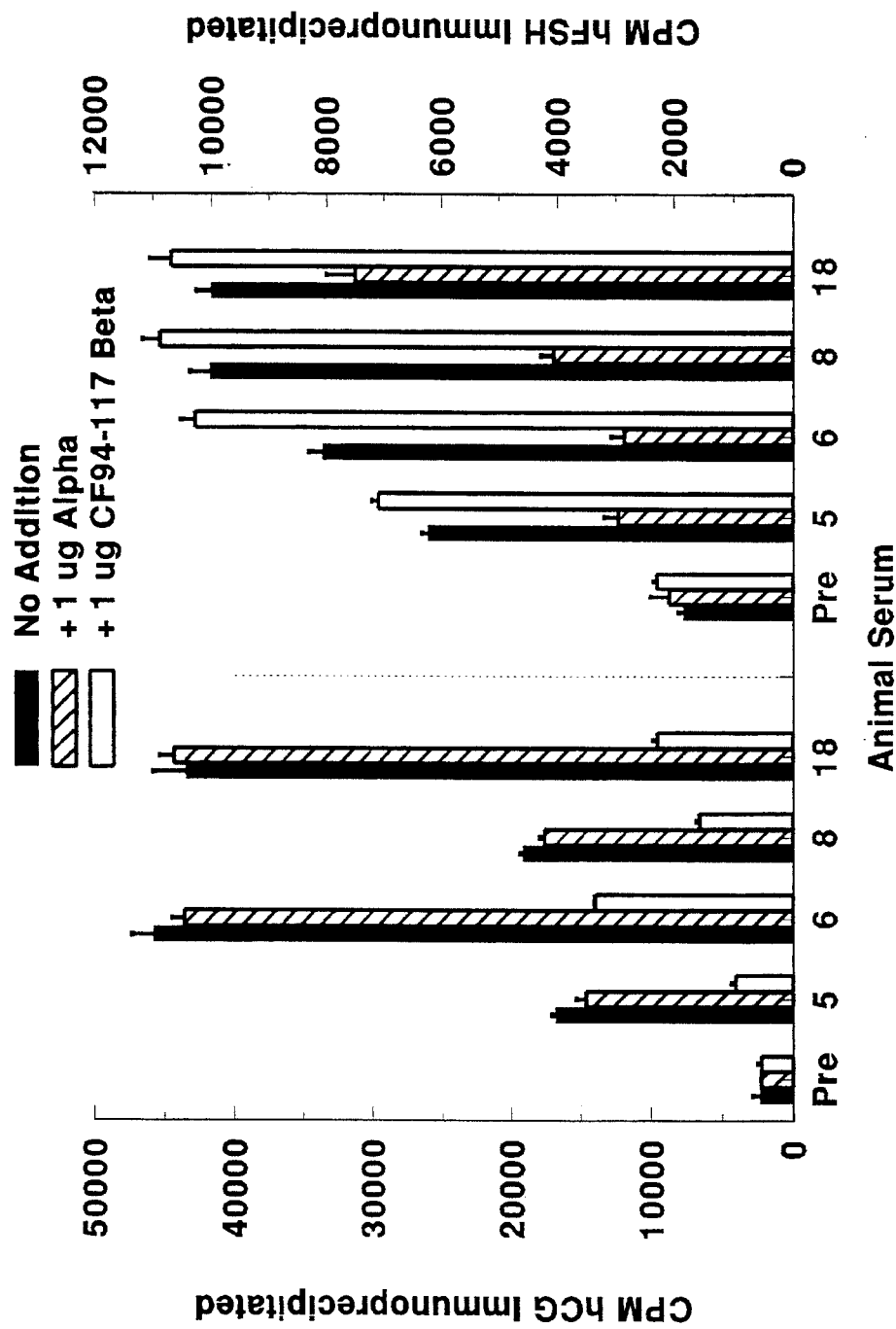
FIG. 8 illustrates the abilities of selected mouse sera to bind to radioiodinated hCG (portion of FIG. 8 to the left of the broken line) or to radioiodinated hFSH (portion of FIG. 8 to the right of the broken line).

As illustrated in FIGS. 7–8, we examined the antigenicity of DG and G in mice. Injection of both analogs into mice elicited the formation of antibodies that had the capacity to bind $^{125}$I-hCG and $^{125}$I-hFSH. The ability to immunoprecipitate hCG is expected since much of the structure of DG is similar to that of hCG (i.e., the sequence of the α-subunit is identical to that of hCG and the sequence of the β-subunit is identical for residues 1–93). The ability to immunoprecipitate hFSH is also expected since both DG and G have the human α-subunit as does hFSH. Indeed, we observed that virtually all of the abilities of the mouse antisera to immunoprecipitate hFSH were eliminated by addition of hCG or human α-subunit. Only one mouse (#18) gave any response to G that would suggest that it made an immune response to the FSH portions of this analog. This suggests that it is unlikely that any of these analogs will be antigenic in women since hCG is not a foreign protein in humans.

APPENDIX OF REFERENCES

1. Yen, S. S. C. and Jaffe, R. B., (1986) "Reproductive Endocrinology: Physiology, Pathophysiology and Clinical Management," 2nd edition, W. B. Saunders Company, Philadelphia (1986).

2. Office of Technology Assessment: Report Brief-Infertility: Medical and Social Choices. Washington, D.C., OTA, US Congress, May 1988.

3. Institute of Medicine and National Research Council, Medically assisted conception: an agenda for research. National Academy Press, Washington, D.C. (1989).

4. Bousfield G. R., and Ward, D. N., (1988) *J. Biol. Chem.* 263, 12602.

5. Rodgers, N., Mitchess, R., Lambert, A., and Robertson, W. R., (1991) *J. Endocrinol.* 129 (Supplement), 111.

6. Harlin, J.,. Kahn, S. A., and Diczfalusy, E,, (1986) *Fertil. Steril.* 46, 1055.

7. Wallach, E. E., (1991) *Fertil. Steril.* 55, 478.

8. Schenker, J. G. and Weinstein, D., (1978) *Fertil. Steril.* 30, 255.

9. Murphy, B. D. and Martinuk, S. D., (1991) *Endocrine Rev.* 12, 27.

10 Campbell, R. K., Dean-Emig, D. M., and Moyle, W. R., (1991) *Proc. Nat'l. Acad. Sci. (USA)* 88, 760.

11. Pierce, J. G. and Parsons, T. F., (1981) *Ann. Rev. Biochem.* 50, 465.

12. Fiddes, J. C. and Goodman, H. M., (1980) *Nature* 286, 684.

13. Fiddes, J. C. and Goodman, H. M., (1979) *Nature* 281, 351.

14. Keutmann, H. T., Charlesworth, M. C., Mason, K. A., Ostrea, T., Johnson, L., and Ryan, R. J., (1987) *Proc. Nat'l. Acad. Sci. (USA)* 84, 2038.

15. Santa Coloma, T. A., and Reichert, L. E., Jr., (1990) *J. Biol. Chem.* 265, 5037.

16. Schneyer, A. L., Sluss, P. M., Huston, J. S., Ridge, R. J., and Reichert, L. E., Jr., (1988) *Biochem.* 27, 666.

17. Reddy, V. B., Beck, A. K., Garramone, A. J., Vellucci, B., Lustbader, J. W., and Bernsteine, E. G., (1985) *Proc. Nat'l. Acad. Sci. (USA)* 82, 14204.

18. Matzuk, M. M., Krieger, M., Corless, C. L., and Boime, I., (1987) *Proc. Natl. Acad. Sci. (USA)* 84, 6354–6358.

19. Matzuk, M. M., Kornmeier, C. M., Whitfield, G. K., Konids, I. A., and Boime, I., (1988) *Molec. Endocrinol.* 95–100.

20. Matzuk, M. M. and Boime, I., (1988) *J. Cell Biol.* 106, 1049–1059.

21. Moyle, W. R., Matzuk, M. M., Campbell, R. K., Cogliani, E., Dean-Emig, D. M., Krichevsky, A., Barnett, R. W., and Boime, I., (1990) *J. Biol. Chem.* 265, 8511.

22. Moyle, W. R., Bahl, O. P., and Marz, L., (1975) *J. Biol. Chem.* 250, 9163.

23. Sambrook, J., Fritsch, E. F., and Maniatis, T., (1989) Molecular Cloning: A laboratory manual (second edition) Cold Spring Harbor Laboratory Press.

24. Ausubel, F. M., Brent, R., Kingston, R. E. Moore, D. D., Seidman, J. G., Smith, J. A., and Struhl, K., (1987) Current Protocols in Molecular Biology. Greene Publishing Associates and Wiley-Interscience, New-York.

25. Moyle, W. R., Anderson, D. M., Macdonald, G. J. and Armstrong, E. G., (1988) J. Receptor Research 8, 419.

The invention being thus described, it will be obvious that the same may be varied in many ways. Such variations are not to be regarded as a departure from the spirit and scope of the invention and all such modifications are intended to be included within the scope of the following claims.

---

We claim:

1. An alpha, beta-heterodimeric polypeptide having binding affinity to vertebrate luteinizing hormone (LH) receptors and vertebrate follicle stimulating hormone (FSH) receptors consisting essentially of a glycoprotein hormone alpha-subunit polypeptide and a non-naturally occurring beta-subunit polypeptide, wherein the beta-subunit polypeptide is a chain of amino acids comprising the following four sequentially joined subsequences:

(a) a first subsequence homologous to the amino acid sequence of residues 1–93 (hCG numbering) of the beta-subunit selected from the group consisting of human chorionic gonadotropin (hCG), vertebrate luteinizing hormone (LH), vertebrate follicle stimulating hormone (FSH), and vertebrate thyroid stimulating hormone (TSH);

(b) a second subsequence homologous to the amino acid sequence of residues 94–97 (hCG numbering) of the beta-subunit selected from the group consisting of human chorionic gonadotrophin (hCG) and vertebrate luteinizing hormone (LH);

(c) a third subsequence homologous to the amino acid sequence of residues 98–100 (hCG numbering) of the beta-subunit selected from the group consisting of human chorionic gonadotrophin (hCG), vertebrate luteinizing hormone (LH), vertebrate follicle stimulating hormone (FSH), and vertebrate thyroid stimulating hormone (TSH); and (d) a fourth subsequence homologous to the amino acid sequence of residues 95–104 (FSH numbering) of the beta-subunit of vertebrate follicle stimulating hormone.

2. The alpha, beta-heterodimeric polypeptide according to claim 1, wherein the glycoprotein hormone alpha-subunit polypeptide is a human alpha-subunit polypeptide.

3. The alpha, beta-heterodimeric polypeptide according to claim 1, wherein the glycoprotein hormone alpha-subunit polypeptide is the alpha-subunit of hCG.

4. The alpha, beta-heterodimeric polypeptide according to claim 1, wherein the first subsequence (a) is homologous to residues 1–93 (hCG numbering) of the beta-subunit of human chorionic gonadotrophin (hCG), the second subsequence (b) is homologous to residues 94–97 (hCG numbering) of the beta-subunit of human chorionic gonadotrolphin (hCG), the third subsequence (c) is homologous to residues 98–100 (hCG numbering) of the beta-subunit of human chorionic gonadotrophin (hCG), and the fourth subsequence (d) is homologous to residues 95–104 (FSH numbering) of the beta-subunit of vertebrate follicle stimulating hormone.

5. A pharmaceutical composition comprising a pharmaceutically acceptable carrier and the alpha, beta-heterodimeric polypeptide according to claim 1.

6. An alpha, beta-heterodimeric polypeptide having greater binding affinity than luteinizing hormone (LH) for vertebrate follicle stimulating hormone (FSH) receptors consisting essentially of a glycoprotein hormone alpha-subunit polypeptide and a non-naturally occurring beta-subunit polypeptide, wherein the beta-subunit polypeptide is a chain of amino acids comprising the following four sequentially joined subsequences:

(a) a first subsequence homologous to the amino acid sequence of residues 1–93 (hCG numbering) of the beta-subunit selected from the group consisting of human chorionic gonadotrophin (hCG), vertebrate luteinizing hormone (LH), vertebrate follicle stimulating hormone (FSH), and vertebrate thyroid stimulating hormone (TSH);

(b) a second subsequence comprising 4 amino acids for residues 94–97 (hCG numbering);

(c) a third subsequence comprising 2 amino acids for residues 98–99 (hCG numbering); and (d) a fourth subsequence homologous to the amino acid sequence of residues 94–104 (FSH numbering) of the beta-subunit of vertebrate follicle stimulating hormone.

7. An alpha, beta-heterodimeric polypeptide having greater binding affinity than luteinizing hormone for follicle stimulating hormone (FSH) receptors consisting essentially of a glycoprotein hormone alpha-subunit polypeptide and a non-naturally occurring beta-subunit polypeptide, wherein the beta-subunit polypeptide is a chimera comprised of amino acids 1–100 of any vertebrate glycoprotein hormone homologous to amino acids found in residues 1–100 of human chorionic gonadotropin and any 1–20 amino acids.

8. The alpha, beta-heterodimeric polypeptide according to claim 6, wherein residues 94–97 are other than Asp-Ser-Asp-Ser.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 145 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:1:

```
Ser  Lys  Glu  Pro  Leu  Arg  Pro  Arg  Cys  Arg  Pro  Ile  Asn  Ala  Thr  Leu
 1                  5                        10                           15

Ala  Val  Glu  Lys  Glu  Gly  Cys  Pro  Val  Cys  Ile  Thr  Val  Asn  Ile  Thr
               20                       25                       30

Ile  Cys  Ala  Gly  Tyr  Cys  Pro  Thr  Met  Thr  Arg  Val  Leu  Gln  Gly  Val
          35                       40                            45

Leu  Pro  Ala  Leu  Pro  Gln  Val  Val  Cys  Asn  Tyr  Arg  Asp  Val  Arg  Phe
     50                       55                       60

Glu  Ser  Ile  Arg  Leu  Pro  Gly  Cys  Pro  Arg  Gly  Val  Asn  Pro  Val  Val
65                       70                       75                       80

Ser  Tyr  Ala  Val  Ala  Leu  Ser  Cys  Gln  Cys  Ala  Leu  Cys  Arg  Arg  Ser
                    85                       90                       95

Thr  Thr  Asp  Cys  Gly  Gly  Pro  Lys  Asp  His  Pro  Leu  Thr  Cys  Asp  Asp
               100                      105                      110
```

```
              Pro  Arg  Phe  Gln  Asp  Ser  Ser  Ser  Lys  Ala  Pro  Pro  Pro  Ser  Leu
                        115                 120                 125

Pro  Ser  Pro  Ser  Arg  Leu  Pro  Gly  Pro  Ser  Asp  Thr  Pro  Ile  Leu  Pro
                        130                 135                 140

Gln
              145
```

( 2 ) INFORMATION FOR SEQ ID NO:2:

( i ) SEQUENCE CHARACTERISTICS:
        ( A ) LENGTH: 145 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:2:

```
              Ser  Lys  Glu  Pro  Leu  Arg  Pro  Arg  Cys  Arg  Pro  Ile  Asn  Ala  Thr  Leu
              1                   5                   10                  15

Ala  Val  Glu  Lys  Glu  Gly  Cys  Pro  Val  Cys  Ile  Thr  Val  Asn  Ile  Thr
                        20                  25                  30

Ile  Cys  Ala  Gly  Tyr  Cys  Pro  Thr  Met  Thr  Arg  Val  Leu  Gln  Gly  Val
                        35                  40                  45

Leu  Pro  Ala  Leu  Pro  Gln  Val  Val  Cys  Asn  Tyr  Arg  Asp  Val  Arg  Phe
                   50                  55                       60

Glu  Ser  Ile  Arg  Leu  Pro  Gly  Cys  Pro  Arg  Gly  Val  Asn  Pro  Val  Val
              65                       70                  75                            80

Ser  Tyr  Ala  Val  Ala  Leu  Ser  Cys  Gln  Cys  Ala  Leu  Cys  Arg  Arg  Ser
                             85                       90                       95

Thr  Thr  Asp  Cys  Gly  Gly  Pro  Lys  Asp  His  Pro  Leu  Thr  Cys  Asp  Asp
                        100                 105                 110

Pro  Arg  Phe  Gln  Asp  Ser  Ser  Ser  Lys  Ala  Pro  Pro  Pro  Ser  Leu
                        115                 120                 125

Pro  Ser  Pro  Ser  Arg  Leu  Pro  Gly  Pro  Ser  Asp  Thr  Pro  Ile  Leu  Pro
                        130                 135                 140

Gln
              145
```

( 2 ) INFORMATION FOR SEQ ID NO:3:

( i ) SEQUENCE CHARACTERISTICS:
        ( A ) LENGTH: 111 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:3:

```
              Asn  Ser  Cys  Glu  Leu  Thr  Asn  Ile  Thr  Ile  Ala  Ile  Glu  Lys  Glu  Glu
              1                   5                        10                  15

Cys  Arg  Phe  Cys  Ile  Ser  Ile  Asn  Ile  Thr  Trp  Cys  Ala  Gly  Tyr  Cys
                        20                  25                       30

Tyr  Thr  Arg  Asp  Leu  Val  Tyr  Lys  Asp  Pro  Ala  Arg  Pro  Lys  Ile  Gln
                        35                  40                       45
```

|     |     |     |     |     |     |     |     |     |     |     |     |     |     |     |
|-----|-----|-----|-----|-----|-----|-----|-----|-----|-----|-----|-----|-----|-----|-----|
| Lys | Thr | Cys | Thr | Phe | Lys | Glu | Leu | Val | Tyr | Glu | Thr | Val | Arg | Val | Pro |
|     | 50  |     |     |     |     | 55  |     |     |     |     | 60  |     |     |     |     |
| Gly | Cys | Ala | His | His | Ala | Asp | Ser | Leu | Tyr | Thr | Tyr | Pro | Val | Ala | Leu |
| 65  |     |     |     |     | 70  |     |     |     |     | 75  |     |     |     |     | 80  |
| Gln | Cys | His | Cys | Gly | Lys | Cys | Asp | Ser | Asp | Ser | Thr | Asp | Cys | Thr | Val |
|     |     |     |     | 85  |     |     |     |     | 90  |     |     |     |     | 95  |     |
| Arg | Gly | Leu | Gly | Pro | Ser | Tyr | Cys | Ser | Phe | Gly | Glu | Met | Lys | Glu |
|     |     |     | 100 |     |     |     |     |     | 105 |     |     |     | 110 |     |

( 2 ) INFORMATION FOR SEQ ID NO:4:

( i ) SEQUENCE CHARACTERISTICS:
        ( A ) LENGTH: 111 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:4:

| Asn | Ser | Cys | Glu | Leu | Thr | Asn | Ile | Thr | Ile | Ala | Ile | Glu | Lys | Glu | Glu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Cys | Arg | Phe | Cys | Ile | Ser | Ile | Asn | Ile | Thr | Trp | Cys | Ala | Gly | Tyr | Cys |
|     |     |     | 20  |     |     |     |     | 25  |     |     |     |     | 30  |     |     |
| Tyr | Thr | Arg | Asp | Leu | Val | Tyr | Lys | Asp | Pro | Ala | Arg | Pro | Lys | Ile | Gln |
|     |     | 35  |     |     |     |     | 40  |     |     |     |     | 45  |     |     |     |
| Lys | Thr | Cys | Thr | Phe | Lys | Glu | Leu | Val | Tyr | Glu | Thr | Val | Arg | Val | Pro |
|     | 50  |     |     |     |     | 55  |     |     |     |     | 60  |     |     |     |     |
| Gly | Cys | Ala | His | His | Ala | Asp | Ser | Leu | Tyr | Thr | Tyr | Pro | Val | Ala | Leu |
| 65  |     |     |     |     | 70  |     |     |     |     | 75  |     |     |     |     | 80  |
| Gln | Cys | His | Cys | Gly | Lys | Cys | Asp | Ser | Asp | Ser | Thr | Asp | Cys | Thr | Val |
|     |     |     |     | 85  |     |     |     |     | 90  |     |     |     |     | 95  |     |
| Arg | Gly | Leu | Gly | Pro | Ser | Tyr | Cys | Ser | Phe | Gly | Glu | Met | Lys | Glu |
|     |     |     | 100 |     |     |     |     |     | 105 |     |     |     | 110 |     |

( 2 ) INFORMATION FOR SEQ ID NO:5:

( i ) SEQUENCE CHARACTERISTICS:
        ( A ) LENGTH: 149 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:5:

| Ser | Arg | Gly | Pro | Leu | Arg | Pro | Leu | Cys | Arg | Pro | Ile | Asn | Ala | Thr | Leu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Ala | Ala | Glu | Lys | Glu | Ala | Cys | Pro | Ile | Cys | Ile | Thr | Phe | Thr | Thr | Ser |
|     |     |     | 20  |     |     |     |     | 25  |     |     |     |     | 30  |     |     |
| Ile | Cys | Ala | Gly | Tyr | Cys | Pro | Ser | Met | Val | Arg | Val | Met | Pro | Ala | Ala |
|     |     | 35  |     |     |     |     | 40  |     |     |     |     | 45  |     |     |     |
| Leu | Pro | Ala | Ile | Pro | Gln | Pro | Val | Cys | Thr | Tyr | Arg | Glu | Leu | Arg | Phe |
|     | 50  |     |     |     |     | 55  |     |     |     |     | 60  |     |     |     |     |
| Ala | Ser | Ile | Arg | Leu | Pro | Gly | Cys | Pro | Pro | Gly | Val | Asp | Pro | Met | Val |
| 65  |     |     |     |     | 70  |     |     |     |     | 75  |     |     |     |     | 80  |

```
      Ser  Phe  Pro  Val  Ala  Leu  Ser  Cys  His  Cys  Gly  Pro  Cys  Gln  Ile  Lys
                          85                       90                           95

Thr  Thr  Asp  Cys  Gly  Val  Phe  Arg  Asp  Gln  Pro  Leu  Ala  Cys  Ala  Pro
                         100                      105                     110

Gln  Ala  Ser  Ser  Ser  Ser  Lys  Asp  Pro  Pro  Ser  Gln  Pro  Leu  Thr  Ser
                    115                      120                     125

Thr  Ser  Thr  Pro  Thr  Pro  Gly  Ala  Ser  Arg  Arg  Ser  Ser  His  Pro  Leu
                130                      135                     140

Pro  Ile  Lys  Thr  Ser
      145
```

( 2 ) INFORMATION FOR SEQ ID NO:6:

( i ) SEQUENCE CHARACTERISTICS:
      ( A ) LENGTH: 112 amino acids
      ( B ) TYPE: amino acid
      ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:6:

```
      Phe  Cys  Ile  Pro  Thr  Glu  Tyr  Met  Thr  His  Ile  Glu  Arg  Arg  Glu  Cys
      1                   5                       10                          15

Ala  Tyr  Cys  Leu  Thr  Ile  Asn  Thr  Thr  Ile  Cys  Ala  Gly  Tyr  Cys  Met
                     20                      25                          30

Thr  Arg  Asp  Ile  Asn  Gly  Lys  Leu  Phe  Leu  Pro  Lys  Tyr  Ala  Leu  Ser
                35                       40                      45

Gln  Asp  Val  Cys  Thr  Tyr  Arg  Asp  Phe  Ile  Tyr  Arg  Thr  Val  Glu  Ile
           50                      55                      60

Pro  Gln  Cys  Pro  Leu  His  Val  Ala  Pro  Tyr  Phe  Ser  Tyr  Pro  Val  Ala
      65                       70                      75                          80

Leu  Ser  Cys  Lys  Cys  Gly  Lys  Cys  Asp  Thr  Asp  Tyr  Ser  Asp  Cys  Ile
                     85                      90                          95

His  Glu  Ala  Ile  Lys  Thr  Asn  Tyr  Cys  Thr  Lys  Pro  Gln  Lys  Ser  Tyr
                    100                     105                     110
```

( 2 ) INFORMATION FOR SEQ ID NO:7:

( i ) SEQUENCE CHARACTERISTICS:
      ( A ) LENGTH: 114 amino acids
      ( B ) TYPE: amino acid
      ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:7:

```
      Ser  Lys  Glu  Pro  Leu  Arg  Pro  Arg  Cys  Arg  Pro  Ile  Asn  Ala  Thr  Leu
      1                   5                       10                          15

Ala  Val  Glu  Lys  Glu  Gly  Cys  Pro  Val  Cys  Ile  Thr  Val  Asn  Ile  Thr
                     20                      25                          30

Ile  Cys  Ala  Gly  Tyr  Cys  Pro  Thr  Met  Thr  Arg  Val  Leu  Gln  Gly  Val
                35                       40                      45

Leu  Pro  Ala  Leu  Pro  Gln  Val  Val  Cys  Asn  Tyr  Arg  Asp  Val  Arg  Phe
           50                      55                      60
```

```
            Glu  Ser  Ile  Arg  Leu  Pro  Gly  Cys  Pro  Arg  Gly  Val  Asn  Pro  Val  Val
            65                  70                       75                            80

Ser  Tyr  Ala  Val  Ala  Leu  Ser  Cys  Gln  Cys  Ala  Leu  Cys  Arg  Arg  Ser
                                85                       90                       95

Thr  Thr  Asp  Cys  Thr  Val  Arg  Gly  Leu  Gly  Pro  Ser  Tyr  Cys  Asp  Asp
                           100                      105                      110

Pro  Arg
```

( 2 ) INFORMATION FOR SEQ ID NO:8:

( i ) SEQUENCE CHARACTERISTICS:
        ( A ) LENGTH: 114 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:8:

```
            Ser  Lys  Glu  Pro  Leu  Arg  Pro  Arg  Cys  Arg  Pro  Ile  Asn  Ala  Thr  Leu
            1                    5                       10                            15

Ala  Val  Glu  Lys  Glu  Gly  Cys  Pro  Val  Cys  Ile  Thr  Val  Asn  Ile  Thr
                                20                       25                       30

Ile  Cys  Ala  Gly  Tyr  Cys  Pro  Thr  Met  Thr  Arg  Val  Leu  Gln  Gly  Val
                           35                       40                       45

Leu  Pro  Ala  Leu  Pro  Gln  Val  Val  Cys  Asn  Tyr  Arg  Asp  Val  Arg  Phe
                 50                       55                       60

Glu  Ser  Ile  Arg  Leu  Pro  Gly  Cys  Pro  Arg  Gly  Val  Asn  Pro  Val  Val
            65                  70                       75                            80

Ser  Tyr  Ala  Val  Ala  Leu  Ser  Cys  Gln  Cys  Ala  Leu  Cys  Asp  Ser  Asp
                                85                       90                       95

Ser  Thr  Asp  Cys  Thr  Val  Arg  Gly  Leu  Gly  Pro  Ser  Tyr  Cys  Ser  Phe
                           100                      105                      110

Gly  Glu
```

( 2 ) INFORMATION FOR SEQ ID NO:9:

( i ) SEQUENCE CHARACTERISTICS:
        ( A ) LENGTH: 114 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:9:

```
            Ser  Lys  Glu  Pro  Leu  Arg  Pro  Arg  Cys  Arg  Pro  Ile  Asn  Ala  Thr  Leu
            1                    5                       10                            15

Ala  Val  Glu  Lys  Glu  Gly  Cys  Pro  Val  Cys  Ile  Thr  Val  Asn  Ile  Thr
                                20                       25                       30

Ile  Cys  Ala  Gly  Tyr  Cys  Pro  Thr  Met  Thr  Arg  Val  Leu  Gln  Gly  Val
                           35                       40                       45

Leu  Pro  Ala  Leu  Pro  Gln  Val  Val  Cys  Asn  Tyr  Arg  Asp  Val  Arg  Phe
                 50                       55                       60

Glu  Ser  Ile  Arg  Leu  Pro  Gly  Cys  Pro  Arg  Gly  Val  Asn  Pro  Val  Val
```

```
                 65                      70                      75                      80
         Ser Tyr Ala Val Ala Leu Ser Cys Gln Cys Ala Leu Cys Asp Ser Asp
                         85                      90                      95

Ser Thr Asp Cys Gly Gly Pro Lys Asp His Pro Ser Tyr Cys Ser Phe
                         100                     105                     110

Gly Glu
```

( 2 ) INFORMATION FOR SEQ ID NO:10:

( i ) SEQUENCE CHARACTERISTICS:
        ( A ) LENGTH: 145 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:10:

```
         Ser Lys Glu Pro Leu Arg Pro Arg Cys Arg Pro Ile Asn Ala Thr Leu
         1               5                       10                      15

Ala Val Glu Lys Glu Gly Cys Pro Val Cys Ile Thr Val Asn Ile Thr
                         20                      25                      30

Ile Cys Ala Gly Tyr Cys Pro Thr Met Thr Arg Val Leu Gln Gly Val
                         35                      40                      45

Leu Pro Ala Leu Pro Gln Val Val Cys Asn Tyr Arg Asp Val Arg Phe
                         50                      55                      60

Glu Ser Ile Arg Leu Pro Gly Cys Pro Arg Gly Val Asn Pro Val Val
         65                      70                      75                      80

Ser Tyr Ala Val Ala Leu Ser Cys Gln Cys Ala Leu Cys Asp Ser Asp
                         85                      90                      95

Ser Thr Asp Cys Gly Gly Pro Lys Asp His Pro Leu Thr Cys Asp Asp
                         100                     105                     110

Pro Arg Phe Gln Asp Ser Ser Ser Ser Lys Ala Pro Pro Pro Ser Leu
                         115                     120                     125

Pro Ser Pro Ser Arg Leu Pro Gly Pro Ser Asp Thr Pro Ile Leu Pro
                         130                     135                     140

Gln
         145
```

( 2 ) INFORMATION FOR SEQ ID NO:11:

( i ) SEQUENCE CHARACTERISTICS:
        ( A ) LENGTH: 117 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:11:

```
         Ser Lys Glu Pro Leu Arg Pro Arg Cys Arg Pro Ile Asn Ala Thr Leu
         1               5                       10                      15

Ala Val Glu Lys Glu Gly Cys Pro Val Cys Ile Thr Val Asn Ile Thr
                         20                      25                      30

Ile Cys Ala Gly Tyr Cys Pro Thr Met Thr Arg Val Leu Gln Gly Val
                         35                      40                      45
```

```
Leu  Pro  Ala  Leu  Pro  Gln  Val  Val  Cys  Asn  Tyr  Arg  Asp  Val  Arg  Phe
     50                      55                      60

Glu  Ser  Ile  Arg  Leu  Pro  Gly  Cys  Pro  Arg  Gly  Val  Asn  Pro  Val  Val
65                      70                      75                           80

Ser  Tyr  Ala  Val  Ala  Leu  Ser  Cys  Gln  Cys  Ala  Leu  Cys  Arg  Arg  Ser
               85                      90                           95

Thr  Thr  Asp  Cys  Ile  His  Glu  Ala  Ile  Lys  Thr  Asn  Tyr  Cys  Thr  Lys
          100                      105                      110

Pro  Gln  Lys  Ser  Tyr
          115
```

( 2 ) INFORMATION FOR SEQ ID NO:12:

( i ) SEQUENCE CHARACTERISTICS:
    ( A ) LENGTH: 117 amino acids
    ( B ) TYPE: amino acid
    ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:12:

```
Ser  Lys  Glu  Pro  Leu  Arg  Pro  Arg  Cys  Arg  Pro  Ile  Asn  Ala  Thr  Leu
1               5                       10                           15

Ala  Val  Glu  Lys  Glu  Gly  Cys  Pro  Val  Cys  Ile  Thr  Val  Asn  Ile  Thr
          20                      25                      30

Ile  Cys  Ala  Gly  Tyr  Cys  Pro  Thr  Met  Thr  Arg  Val  Leu  Gln  Gly  Val
          35                      40                      45

Leu  Pro  Ala  Leu  Pro  Gln  Val  Val  Cys  Asn  Tyr  Arg  Asp  Val  Arg  Phe
     50                      55                      60

Glu  Ser  Ile  Arg  Leu  Pro  Gly  Cys  Pro  Arg  Gly  Val  Asn  Pro  Val  Val
65                      70                      75                           80

Ser  Tyr  Ala  Val  Ala  Leu  Ser  Cys  Lys  Cys  Gly  Lys  Cys  Asp  Thr  Asp
               85                      90                           95

Tyr  Ser  Asp  Cys  Ile  His  Glu  Ala  Ile  Lys  Thr  Asn  Tyr  Cys  Thr  Lys
          100                      105                      110

Pro  Gln  Lys  Ser  Tyr
          115
```